(12) United States Patent
Reed

(10) Patent No.: US 7,427,495 B2
(45) Date of Patent: Sep. 23, 2008

(54) METHODS OF USING BCL-2 FOR THE THERAPEUTIC TREATMENT AND PREVENTION OF DISEASES

(75) Inventor: John C. Reed, Carlsbad, CA (US)

(73) Assignee: La Jolla Cancer Research Foundation, La Jolla, CA (US)

( * ) Notice: Subject to any disclaimer, the term of this patent is extended or adjusted under 35 U.S.C. 154(b) by 336 days.

(21) Appl. No.: 10/285,853

(22) Filed: Nov. 1, 2002

(65) Prior Publication Data

US 2003/0069201 A1 Apr. 10, 2003

Related U.S. Application Data

(60) Continuation of application No. 08/625,761, filed on Mar. 29, 1996, now abandoned, which is a division of application No. 08/066,556, filed on May 26, 1993, now Pat. No. 5,550,019.

(51) Int. Cl.
*C12P 21/08* (2006.01)
*C12N 5/20* (2006.01)
*C12N 5/24* (2006.01)

(52) U.S. Cl. .................... 435/70.21; 435/326; 435/334; 435/455; 435/69.6; 800/18

(58) Field of Classification Search .............. 435/70.21, 435/326, 334, 455, 69.6; 800/18
See application file for complete search history.

(56) References Cited

U.S. PATENT DOCUMENTS

| | | | | |
|---|---|---|---|---|
| 4,271,145 A | * | 6/1981 | Wands et al. .............. | 435/70.21 |
| 4,997,764 A | | 3/1991 | Favera | |
| 5,024,947 A | | 6/1991 | Inlow et al. | |
| 5,149,628 A | | 9/1992 | Croce .............................. | 435/6 |
| 5,202,429 A | | 4/1993 | Tsujimoto et al. .............. | 536/23 |
| 5,328,844 A | | 7/1994 | Moore | |

FOREIGN PATENT DOCUMENTS

| | | |
|---|---|---|
| WO | WO 92/22640 | 12/1992 |
| WO | WO 93/20200 | 10/1993 |

OTHER PUBLICATIONS

Deonarain et al. (1998) Exp. Opin. Ther. Pat., vol. 8 (1), 53-69.*
Miller et al. (1995) FASEB, vol. 9, 190-199.*
Stites et al. (1982) Basic & Clinical Immunology, 4th Ed., Chapter 22, pp. 362-363.*
Nunez et al. (1989) PNAS, vol. 86, 4589-4593.*
Strasser et al. (1991) PNAS, vol. 88, 8661-8665.*
Pettersson et al. (1992) Blood, vol. 79 (2), 495-502.*
Anton et al., "Use of the anti-apoptotic gene *BCL-2* in neural transplantation," *Society for Neuroscience Abstracts* 19:1053 (1993).
Behl et al., "BCL-2 prevents killing of neuronal cells by glutamate but not by amyloid β protein," *Biochem. & Biophys. Res. Comm.* 197:949-956 (1993).

Cheung et al., "The tyrosine kinase LCK is critically involved in the growth transformation of human B lymphocytes," *J. Biol. Chem.* 266:8667-8670 (1991).
Cleary et al., "Cloning and structural analysis of cDNAs for Bcl-2 and a hybrid Bcl-2 /immunoglobulin transcript resulting from the t(14;18) translocation," *Cell* 47:19-28 (1986).
Clem et al., "Prevention of apoptosis by a Baculovirus gene during infection of insect cells," *Science* 324:1388-1390 (1991).
Coghlan, "Gene dream fades away," *New Sci.* 148:14-15 (1995).
Donahue et al., "Helper virus induced T cell lymphoma in nonhuman primates after retroviral mediated gene transfer," *J. Exp. Med.* 176:1125-1135 (1992).
Dunphy et al., "Mitosis-inducing factors are present in a latent form during interphase in the Xenopus embryo," *J. Cell. Biol.* 106:2047-2056 (1988).
Franceschi, "Cell proliferation, cell death and aging," *Aging*, 1:3-15 (1989).
Garcia et al., "Prevention of programmed cell death of sympathetic neurons by the Bcl-2 proto-oncogene," *Science* 258:302-304 (1992).
Goodrich et al., "Abrogation by c-myc on G1 phase arrest induced by RB protein but not by p53," *Nature* 360:177-179 (1992).
Grogg et al., "CD4+ T cell-mediated killing of major histocompatibility complex class II-positive antigen-presenting cells (APC) III," *Eur. J. Immunol.* 22:267-272 (1992).
Harlow and Lane, *Antibodies: A Laboratory Manual* (Cold Spring Harbor Laboratory, 1988), p. 203 and 277-280.
Henderson et al., "Induction of Bcl-2 expression by Epstein-Barr virus latent membrane protein 1 protects infected B cells from programmed cell death," *Cell* 65:1107-1115 (1991).
Hockenberry et al., "Bcl-2 is an inner mitochondrial membrane protein that blocks programmed cell death," *Nature* 348:334-336 (1990).
Huang et al., "Suppression of the neoplastic phenotype by replacement of the RB gene in human cancer cells," *Science* 242:1563-1566 (1988).
Itoh et al., "Overexpression of bcl-2, apoptosis suppressing gene: Prolonged viable culture period of hybridoma and enhanced antibody production," *Biotechnology and Bioengineering* 48:118-122 (1995).

(Continued)

*Primary Examiner*—Anne Marie S Wehbe
(74) *Attorney, Agent, or Firm*—McDermott Will & Emery LLP

(57) ABSTRACT

The invention provides a method of treating a disease or pathological condition resulting in apoptotic cell death. The method includes increasing the activity of Bcl-2 in cells affected by the disease or pathological condition. Diseases or pathological conditions can include, for example, neurodegenerative diseases, cancer and viral infections. Also provided is a method of prolonging the in vivo survival of transplanted cells for the treatment of a disease or pathological condition. The method includes increasing the activity of Bcl-2 in a population of cells and transplanting the population of cells having increased Bcl-2 activity into a subject. Diseases or pathological conditions can include, for example, neurodegenerative diseases, cancer and viral infections. A method to enhance the sensitivity of malignant cells to therapy is provided that includes decreasing the activity of Bcl-2 in the malignant cells. Methods to identify compounds that alter apoptotic cell death and to enhance monoclonal antibody production are also provided by the invention disclosed herein.

12 Claims, 16 Drawing Sheets

OTHER PUBLICATIONS

Karson et al., "Prospects for human gene therapy," *J. Rep. Med.* 37:508-514 (1992).

Katsumata et al., "Differential effects of Bcl-2 on T and B cells in transgenic mice," *Proc. Natl. Acad. Sci. USA* 89:11376-11380 (1992).

Ledley, "Clinical considerations in the design of protocols for somatic gene therapy," *Human Gene Therapy* 2:77-83 (1991).

Levine et al., "Conversion of lytic to persistent alphavirus infection by the Bcl-2 cellular oncogene," *Nature* 361:739-742 (1993).

Marshall, "Gene therapy's growing pains," *Science* 269:1050,1052-1055 (1995).

McDonnell and Korsmeyer, "Progression from lymphoid hyperplasia to high-grade malignant lymphoma in mice transgenic for the t(14;18)," *Nature* 349:254-256 (1991).

Miyashita et al., "Bcl-2 gene transfer increases relative resistance of s49.1 and WEHI7.2 lymphoid cells to cell death and DNA fragmentation induced by glucocorticoids and multiple chemotherapeutic drugs," *Cancer Res.* 52:5407-5411 (1992).

Miyashita et al., "Bcl-2 oncoprotein blocks chemotherapy-induced apoptosis in a human leukemia cell line," *Blood* 81:151-157 (1993).

Newmeyer et al., "Egg extracts for nuclear import and nuclear assembly reactions," *Methods in Cell Biology* 36:607-634 (1991).

Orkin, "Hematopoiesis: how does it happen?" *Curr. Opin. Cell. Biol.* 7:870-877 (1995).

Perlmutter et al., "Structure and expression of LCK transcripts in human lymphoid cells," *J. Cell. Biochem.* 38:117-126 (1988).

Potter, "Neoplastic development in B-lymphocytes," *Carcinogenesis* 11:1-13 (1990).

Raff, "Social controls on cell survival and cell death," *Nature* 356:397-400 (1992).

Reed et al., "Antisense-mediated inhibition of BCL2 protooncogene expression and leukemic cell growth and survival: Comparisons of phosphodiester and phosphorothioate oligodeoxynucleotides," *Cancer Res.* 50:6565-6570 (1990).

Schwartzman et al., "Internucleosomal deoxyribonucleic acid cleavage activity in apoptotic thymocytes: Detection and endocrine regulation," *Endocrinology* 128:1190-1197 (1991).

Sentman et al., "Bcl-2 inhibits multiple forms of apoptosis but not negative selection in thymocytes," *Cell* 67:879-888 (1991).

Sinkovics et al., "Apoptosis by genetic engineering," *Leukemia* 8:98-102 (1994).

Strasser et al., "Bcl-2 transgene inhibits T cell death and perturbs thymic self-censorship," *Cell* 67:889-899 (1991).

Vaux et al., "Bcl-2 gene promotes haemopoietic cell survival and cooperates with c-myc to immortalize pre-B cells," *Nature* 335:440-442 (1988).

Vaux, "Toward an understanding of the molecular mechanisms of physiological cell death," *Proc. Natl. Acad. Sci. USA* 90:786-789 (1993).

Williams, "Programmed cell death: Apoptosis and oncogenesis," *Cell* 65:1097-1098 (1991).

Yang, "Gene transfer into mammalian somatic cells in vivo," *Critical Rev. in Biotech.* 12:335-356 (1992).

Yunis et al., "Bcl-2 and other genomic alterations in the prognosis of large-cell lymphoma," *New England Journal of Medicine* 320:1047-1054 (1989).

Ebert et al., "A Moloney MLV-rat somatotropin fusion gene produces biologically active somatotropin in a transgenic pig," *Mol. Endocrinol.*, 2(3):277-283 (1988).

Hammer et al., "Genetic engineering of mammalian embryos," *J. Anim. Sci.*, 63(1):269-278 (1986).

Kappel et al., "Regulating gene expression in transgenic animals," *Curr. Opin. Biotechnol.*, 3(5):548-553 (1992).

Strojek et al., "The use of transgenic animal techniques for livestock improvement," *Genetic Engineering: Principles and Methods*, 10:221-246 (1988).

Tsujimoto et al., "Analysis of the structure, transcripts, and protein products of bcl-2, the gene involved in human follicular lymphoma," *Proc. Natl. Acad. Sci. U. S. A.*, 83(14):5214-5218 (1986).

Wall, "Transgenic livestock: Progress and prospects for the future," *Theriogenology*, 45(1):57-68 (1996).

Lazebnik et al., "Nuclear events of apoptosis in vitro in cell-free mitotic extracts: a model system for analysis of the active phase of apoptosis," *J. Cell Biol.* 123:7-22 (1993).

Wood and Earnshaw, "Mitotic chromatic condensation in vitro using somatic cell extracts and nuclei with variable levels of endogenous topoisomerase II," *J. Cell. Biol.* 111:2839-2850 (1990).

Hennet, et al. "Expression of BCL-2 Protein Enhances the Survival of Mouse Fibrosarcoid Cells in Tumor Necrosis Factor-mediated Cytotoxicity," *Cancer Res.* 53:1456-1460 (1993).

Sinkovics, J.E. "Programmed cell death (apoptosis): its virological and immunological connections (a review)," *Acta Microbiologica Hungarica*, vol. 38(3-4):321-334 (1991).

Wood and Earnshaw, "Mitotic chromatic condensation in vitro using somatic cell extracts and nuclei with variable levels of endogenous topoisomerase II," *The Rockefeller University Press*, 111:2839-2850 (1990).

\* cited by examiner

METHODS OF USING BCL-2 FOR THE THERAPEUTIC TREATMENT AND PREVENTION OF DISEASES

This application is a continuation of application Ser. No. 08/625,761, filed Mar. 29, 1996, now abandoned, which is a divisional of application Ser. No. 08/066,556, filed May 26, 1993, now U.S. Pat. No. 5,550,019.

BACKGROUND OF THE INVENTION

Apoptosis is the term used to describe a type of cellular death that occurs in many tissues as a normal physiological process. Also called "programmed cell death," this form of cellular demise involves the activation in cells of a built-in genetic program for cell suicide by which cells essentially autodigest. The remnants of these dead cells are then cleared almost without a trace by neighboring phagocytic cells, without resulting in inflammation or scarring. Apoptosis thus stands in marked contrast to cell death caused, for example, by oxygen-deprivation in the settings of myocardial infarction or stroke, where cells lose their energy supplies, rupture and spill their contents into the extracellular milieu.

In addition to the normal physiological process where cells are turned over within the body, apoptosis can be induced to occur by cellular, hormonal or other stimuli to remove unwanted cells from the body. For example, killing of tumor cells and virus-infected cells by the immune system's cytolytic T-cells occurs via apoptosis following target recognition. Apoptosis also occurs via loss of hormonal stimulation in the female reproductive tissues with each menstrual cycle in the absence of a successful pregnancy. Further, numerous studies have shown that apoptosis accounts for cell death in a wide variety of clinically important areas. For example, essentially all chemotherapeutic drugs currently used in the treatment of cancer, as well as x-irradiation in many cases, ultimately kill malignant cells by activating intracellular pathways leading to apoptosis.

In contrast to the effect of apoptosis in normal cellular phenomenon, when aberrantly regulated, the death of cells through apoptosis can lead to a variety of disease states and pathological conditions. For example, the death of neurons that occurs in diseases such as Alzheimer's dementia and Parkinson's disease shows many hallmarks of apoptosis. Autoimmune diseases, where immune cells inappropriately attack normal tissues, is due, in part, to a failure of apoptosis to occur. Additionally, cell death caused by viral infection can occur through apoptosis in many cases, including T-cell death induced by the Human Immunodeficiency Virus (HIV) that causes AIDS. In contrast to the induction of apoptosis caused by some viruses, other viruses inhibit this process through the expression of gene products that block apoptosis. Herpes Simplex virus is a specific example of this inhibition where the prevention of apoptosis is necessary for its characteristic persistent or "latent" viral infection.

Efforts have been made using conventional chemotherapy to treat many of the disease states that result in inappropriate apoptotic cell death, including all of those mentioned above, but have so far yielded only minor progress toward an effective treatment. Additionally, other non-conventional approaches have also been tried in specific enhances. For example, Parkinson's disease has been treated in humans using fetal neural tissue transplantation. Extensive testing of such neural tissue transplants as well as testing of genetically engineered fibroblasts has been investigated in animal models of Parkinson's and Alzheimer's disease. In the latter case, fibroblasts were modified to secrete neurotrophic factors such as nerve growth factor(NGF) or neurotransmitters such as precursors of dopamine to prolong recipient neural cell survival. The general difficulty of these treatments is that either only a small number of the transplanted cells initially survive upon implantation, or in the case of genetically-engineered fibroblasts, many of the cells that initially survive fail to continue long-term in vivo survival.

As mentioned previously, cancer chemotherapy acts through a variety of intracellular targets which culminate in the activation of the apoptotic pathway. Cancer is the second leading cause of death in the United States. One out of every 3 Americans will develop some form of this disease in his or her lifetime, and the vast majority will die as a direct result of their malignancies, primarily because of the inadequacy of currently available chemotherapeutic drugs or the spontaneous resistance of malignant cells to such treatments.

Although many details of malignancies are not fully understood, the basis of a variety of cancers have been worked out in large part. For example, the unregulated expression of many genes is now known to cause oncogenic transformation. These genes have generically been termed oncogenes because of their transformation ability when abnormally expressed. Typical examples of such oncogenes include protein kinases such as Src, Herb-2 (NEU), and BCR/ABL, GTPases such as Ki-RAS, Ha-RAS, and N-RAS, and transcription factors such as Fos, Jun and Myc. These and other oncogenes have been well documented to be a major cause in the malignant phenotype of cancers such as neuroblastoma (N-myc), Burkitt lymphoma (c-myc), colorectal carcinoma (Ki-RAS), chronic myelogenous leukemia (BCR/ABL), breast cancer (Herb-2/NEU), and lung cancer (L-myc). Attempts have been made to target several of these oncogenes to provide a therapeutic treatment for the relevant cancer. However, because of the problems mentioned above in regard to chemotherapy, such attempts all too often have proven to be of marginal benefit.

In contrast to oncogenes whose abnormal or unregulated expression results in increased proliferation, there is at least one "oncogene" whose overexpression results in prolonged cell survival. This oncogene is termed Bcl-2 and was originally discovered because of its inappropriate activation in lymphomas, cancers of the lymph nodes, where it contributes to neoplastic cell expansion. High levels of Bcl-2 protein have been demonstrated to occur in approximately 50,000 new cases of lymphoma and leukemia each year in the United States alone, essentially all cases of drug-resistant prostate cancer (150,000 cases per year in USA), 80% of nasopharyngeal carcinomas, about 70% of breast cancers (approximately 100,000 cases per year in the United States) and all cases of colorectal carcinoma examined to date (110,000 new cases per year in USA).

Since its initial discovery, it has been shown that Bcl-2 is also normally expressed in many tissues of the body, where it serves a physiological role of maintaining the survival of long-lived cells. Among the types of cells whose survival Bcl-2 regulates are the "memory" lymphocytes that are generated during immunizations, many types of neurons in the brain and particularly in the peripheral nerves that control muscle and organ functions, bone marrow cells, skin, and the stem cells giving rise to the absorptive cells that line the gastrointestinal tract.

From the foregoing discussion, it is apparent that for many of the diseases that impact the human species, there have been no major advances toward an effective treatment within the last 10 to 15 years. However, as diverse as these diseases and their treatments are, there has developed one common mechanism by which they manifest their characteristics or by which chemotherapy has been rendered ineffectual. This common mechanism is either the induction or inhibition of programmed cell death.

Thus, there exists a need to control the process of apoptosis in order to generically treat a broad range of diseases and pathological conditions, and also to be able to augment clinical treatments employing readily available drugs. The present invention satisfies this need and provides related advantages as well.

SUMMARY OF THE INVENTION

The invention provides a method of treating a disease or pathological condition resulting in apoptotic cell death. The method includes increasing the activity of Bcl-2 in cells affected by the disease or pathological condition. Diseases or pathological conditions can include, for example, neurodegenerative diseases, cancer and virus infected cells. Also provided is a method of prolonging the in vivo survival of transplanted cells for the treatment of a disease or pathological condition. The method includes increasing the activity of Bcl-2 in a population of cells and transplanting the population of cells having increased Bcl-2 activity into a subject. Diseases or pathological conditions can include, for example, neurodegenerative diseases, cancer and virus infected cells. A method to enhance the sensitivity of malignant or virus infected cells to therapy is provided that includes decreasing the activity of Bcl-2 in the malignant or virus infected cells. Methods to identify compounds that alter apoptotic cell death and to enhance monoclonal antibody production are also provided by the invention disclosed herein as well as by using transgenic mice expressing Bcl-2 as the transgene.

A. Cloned human DNA sequences encoding either the full length Bcl-2 protein ("bcl-2α") or a shorter inhibitory form of Bcl-2 ("bcl-2β") were inserted into the unique XhoI site in pBC140 in both the forward and reverse (AS; antisense) orientations. Bcl-2 expression is driven by a cytomegalovirus promoter/enhancer (CMV; black bars). Neomycin phosphotransferase (Neo$^r$) gene expression was driven by the leftmost Moloney virus long terminal repeat (LTR; white bars) and used as a dominant selectable marker using the antibiotic G418. Selected restriction sites are indicated.

B. A human Bcl-2 cDNA encoding the full length Bcl-2 protein was cloned into the unique BamHI site in pZip-NEO. Selected restriction sites are indicated: X, XhoI; Xb, XbaI; B, BamHI. Bcl-2 expression driven by the leftmost Moloney virus LTR. Expression of the neomycin resistance gene is mediated via a splicing event (not shown).

Figure 2A:
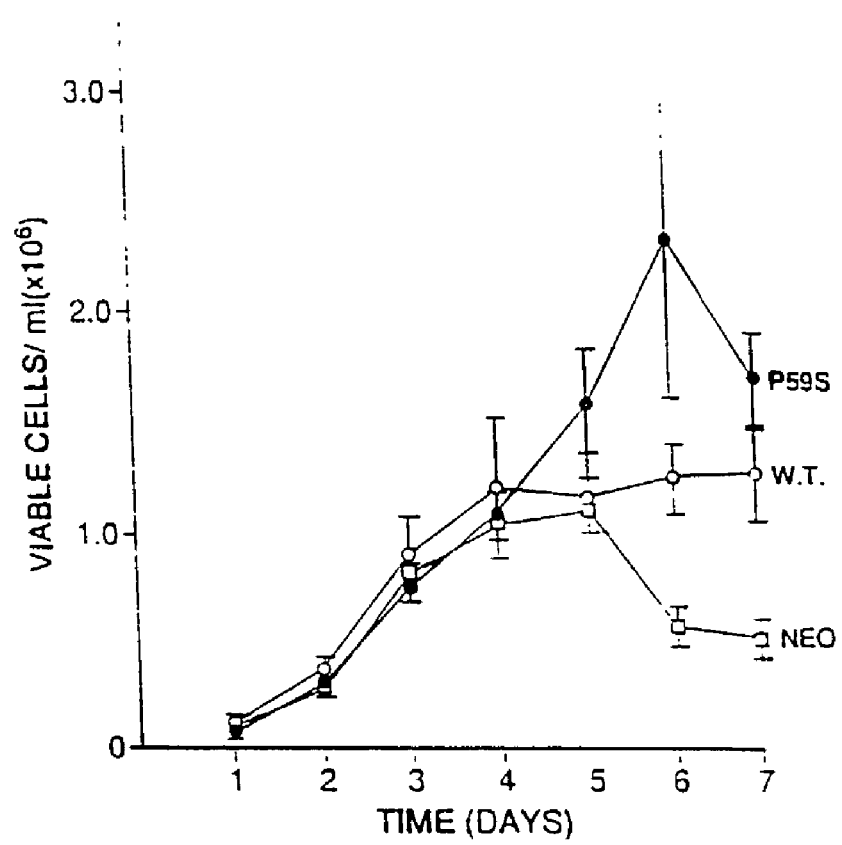
Figure 2B:
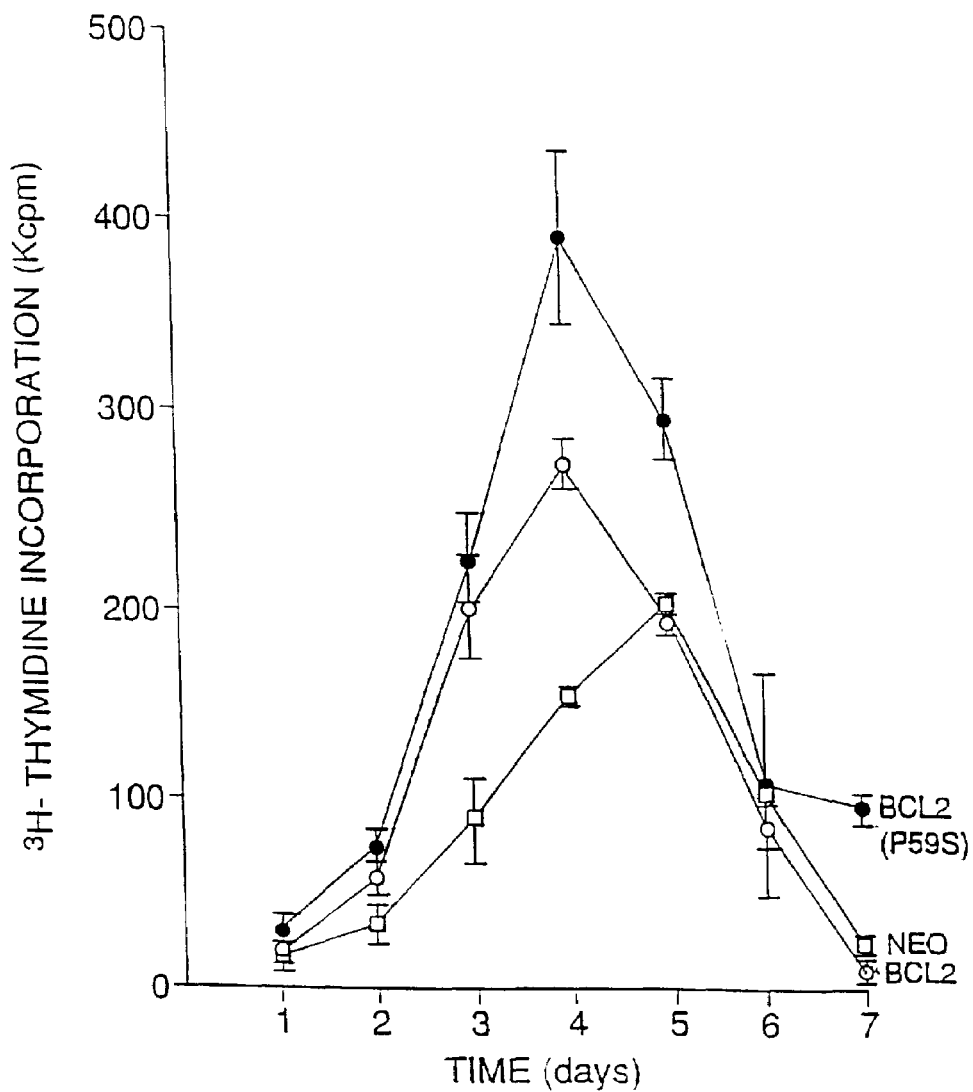

FIG. 2. Bcl-2 and a mutant Bcl-2 (59 Pro->Ser) protein allow mammalian cells to grow to higher cell densities.

A. Cell viability as determined by trypan blue exclusion (mean +/− standard deviation of 3 determinations). W.T., wild-type Bcl-2; P59S, mutant Bcl-2; Neo, control.

B. DNA synthesis as determined by liquid scintillation counting of cells pulse-labeled for 8 hours with $^3$H-thymidine. Kcpm=kilocounts/min (mean +/− standard deviation of 3 determinations).

Figure 3:
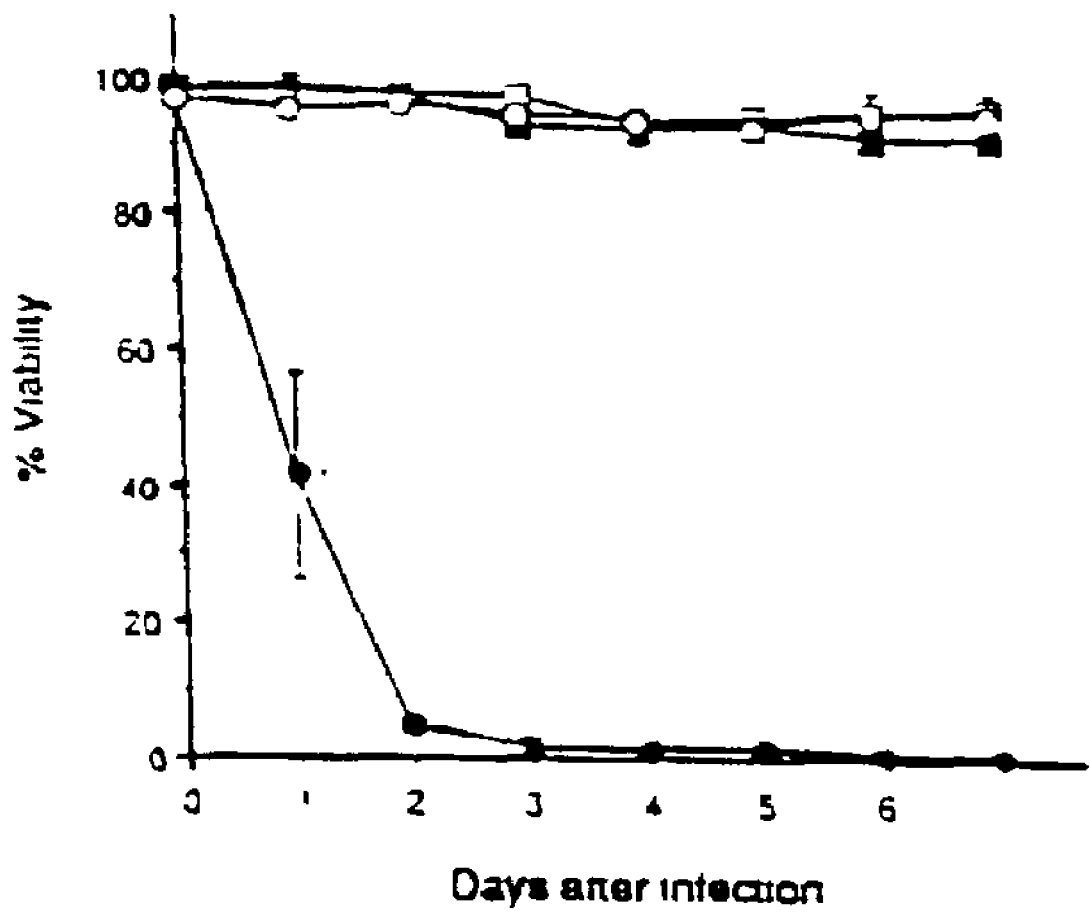

FIG. 3. Bcl-2 blocks prostate cancer cell line, AT-3, death induced by Sindbis virus infection. Cell viability as determine by trypan blue exclusion (mean +/− standard deviation of 3 determinations). pZIP-BCL2 or pZIP-NEO are described in FIG. 1.B. AT-3-NEO control cells (circles); AT-3-BCL2 cells (squares). Virus infected cells (solid symbols); cells cultured in the absence of virus (open symbols).

Figure 4:
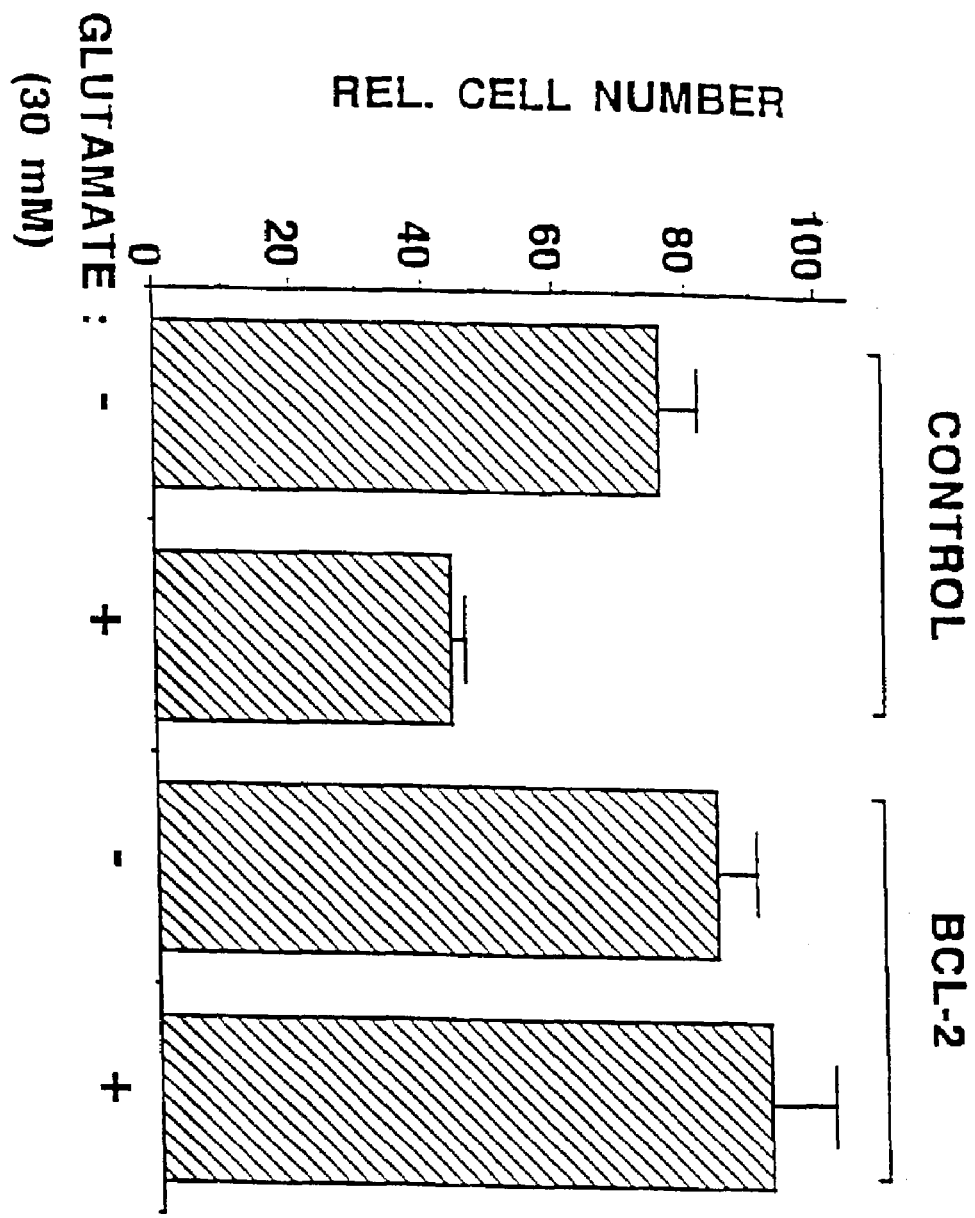

FIG. 4. Protection of PC12 cells from glutamate-induced death by Bcl-2. Cell viability as determined by MTT dye reduction assay (mean +/− standard deviation of 3 determinations).

Figure 5A:
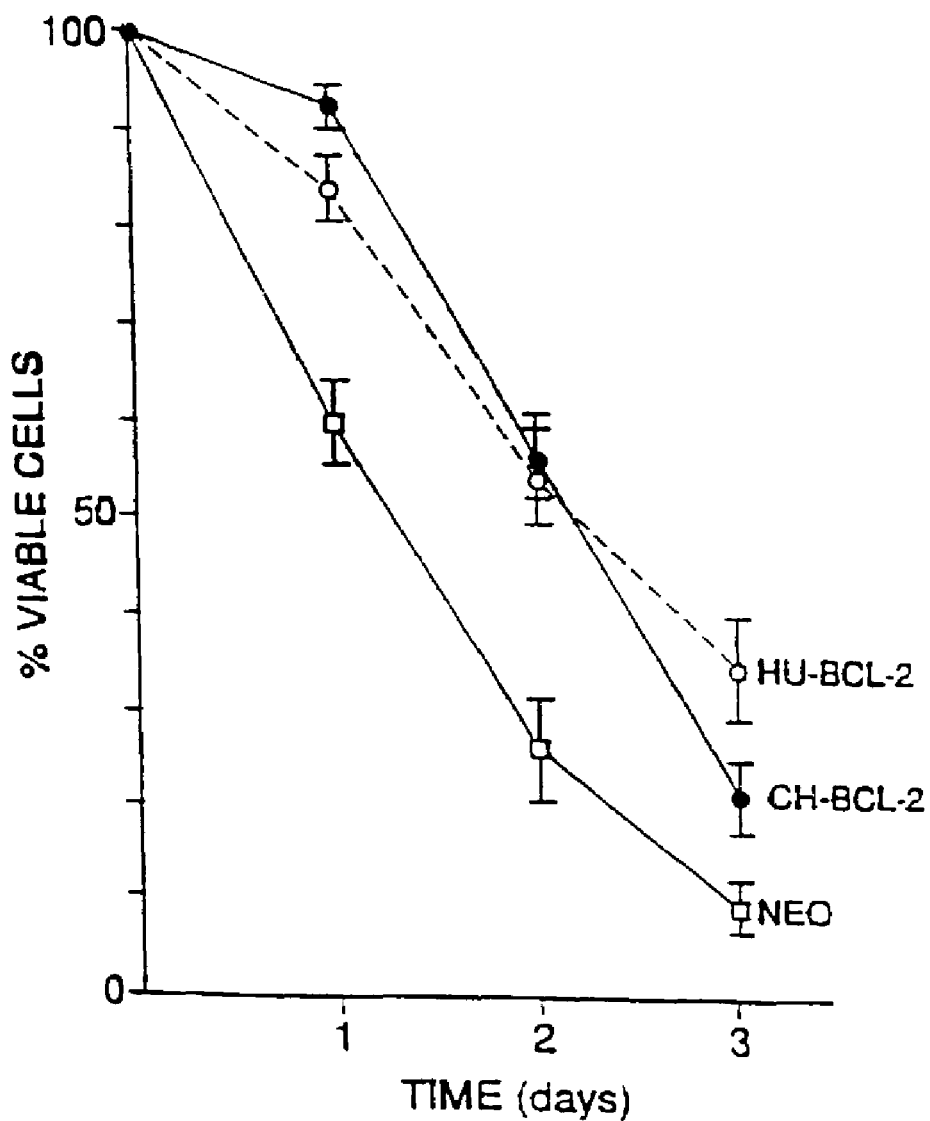
Figure 5B:
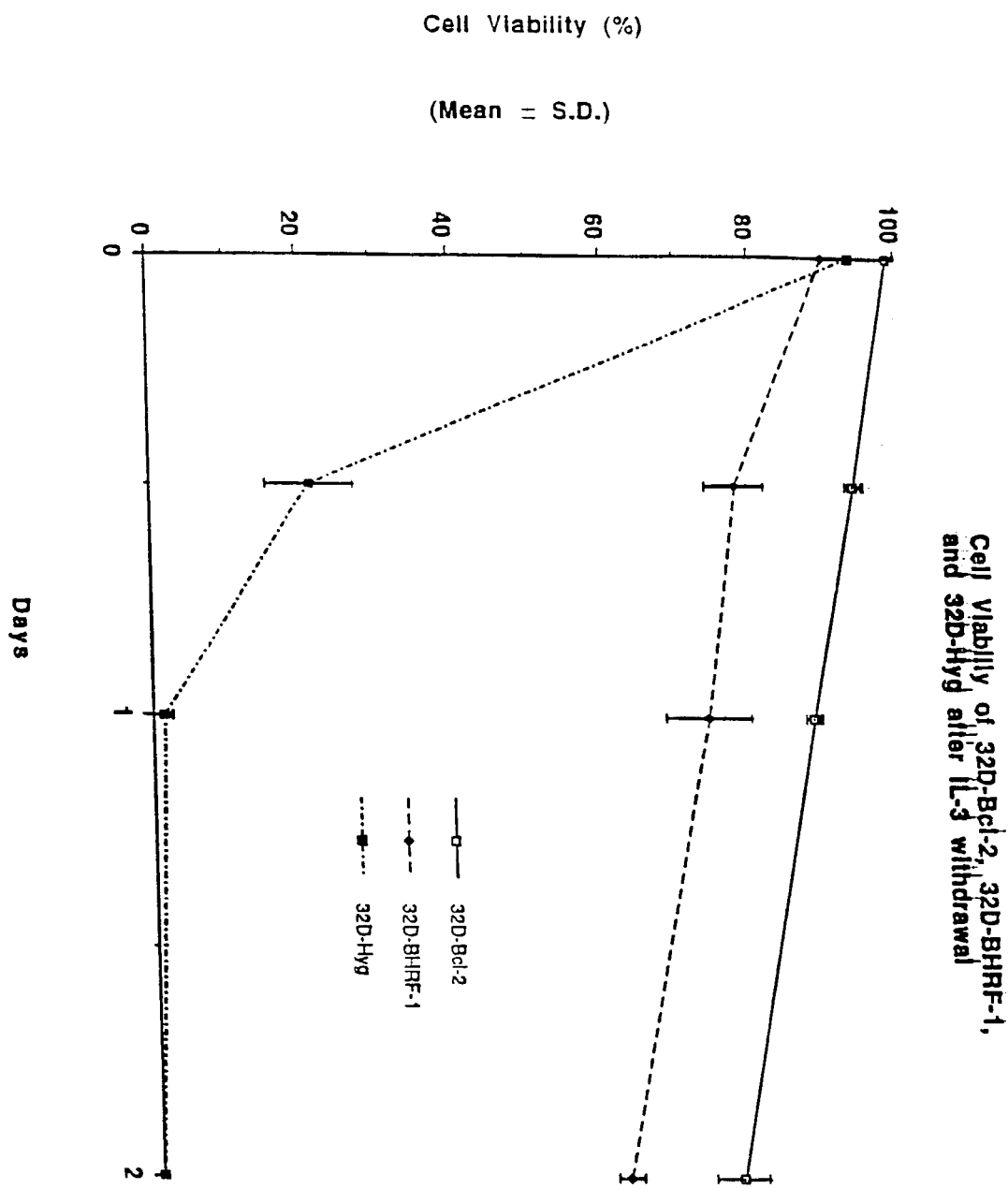

FIG. 5. Homologs of Bcl-2 prolong survival of 32D-3 cells grown in the absence of Il-3 for various times. Cell viability as determined by the trypan blue exclusion (mean +/− standard deviation of 3 determinations).

A. Human (HU) and chicken (CH) Bcl-2 proteins prolong cell survival. (NEO=control; no Bcl-2).

B. Human Bcl-2 and the Epstein Barr virus Bcl-2 homolog, BHRF-1, prolong cell survival. (HYG=control; hygromycin B).

Figure 6A:
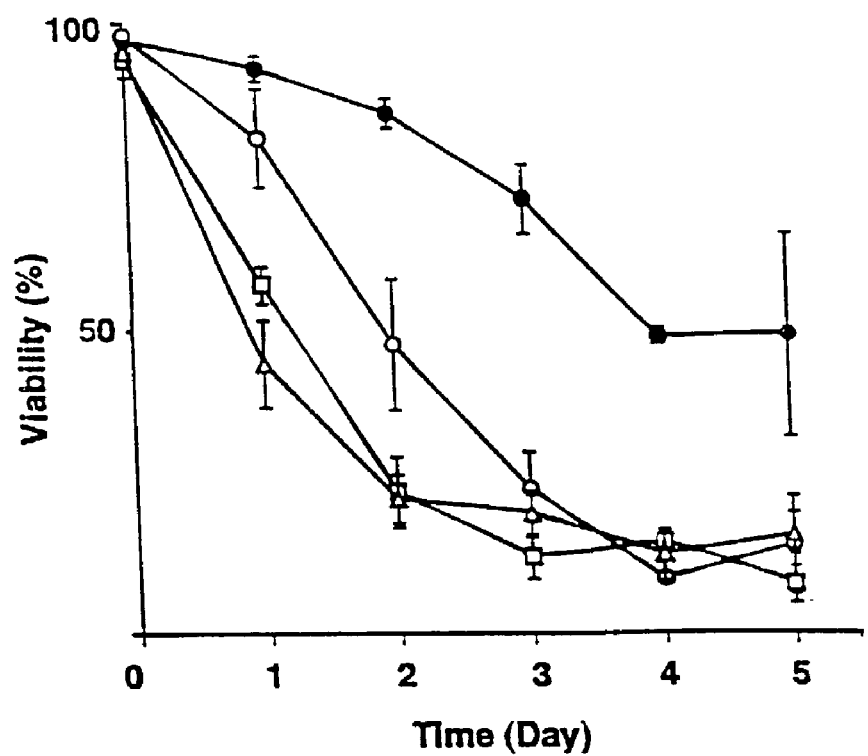
Figure 6B:
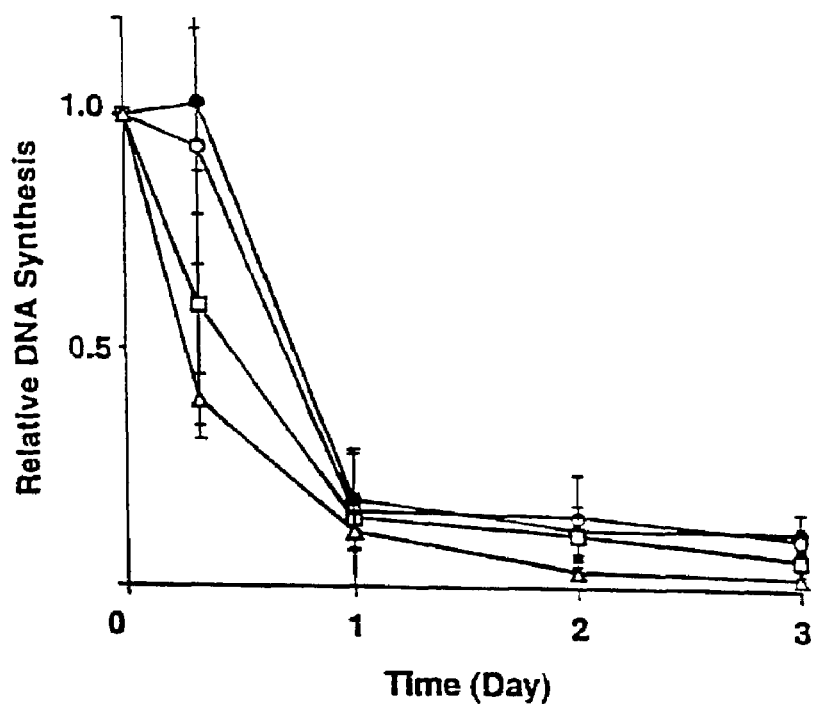
Figure 6C:
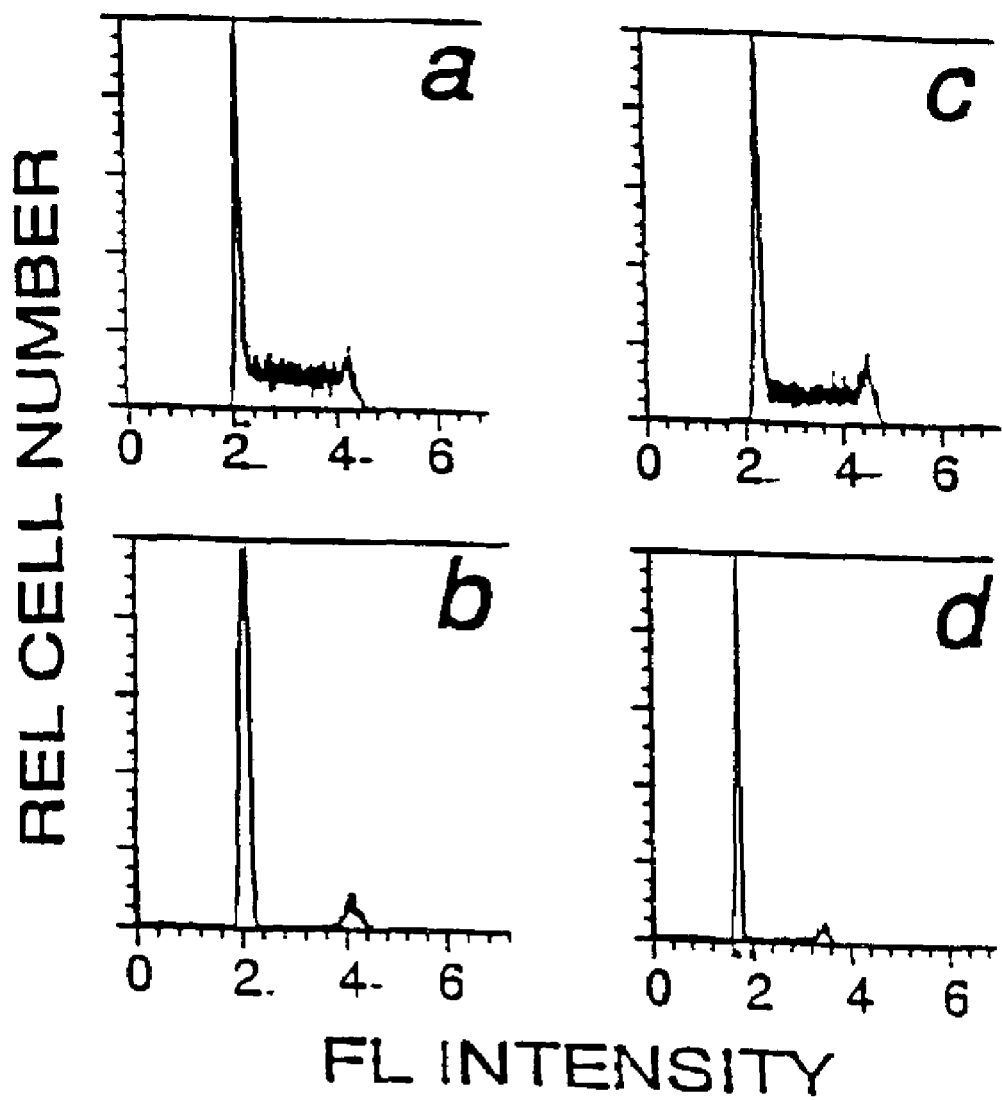

FIG. 6. Bcl-2 acts synergistically with Raf-1 to prolong cell survival under conditions of growth factor deprivation. Bcl-2 protein, alone (open circles); activated Raf-1 protein, alone (squares) Bcl-2+Raf-1 proteins (closed circles); no Bcl-2 or Raf-1 protein (triangles).

A. Cell viability as determined by trypan blue exclusion (mean +/− standard deviation of 3 determinations).

B. DNA synthesis as determined by 3H-thymidine incorporation. Data were normalized by dividing the results obtained for cells cultured in the absence of interleukin-3 (Il-3) by values obtained for cells cultured in the presence of Il-3 (mean +/−standard deviation of 3 determinations).

C. Relative DNA content of propidium-iodide-stained viable cells as determined by flow cytometry. Cells were grown for 3 days in the presence (panels a and c) or absence (panels b and d) of Il-3. 32D-BCL2 cells (panels a and b); 32-D-BCL2/RAF cells (panels c and d). (FL=fluorescence intensity).

Figure 7:
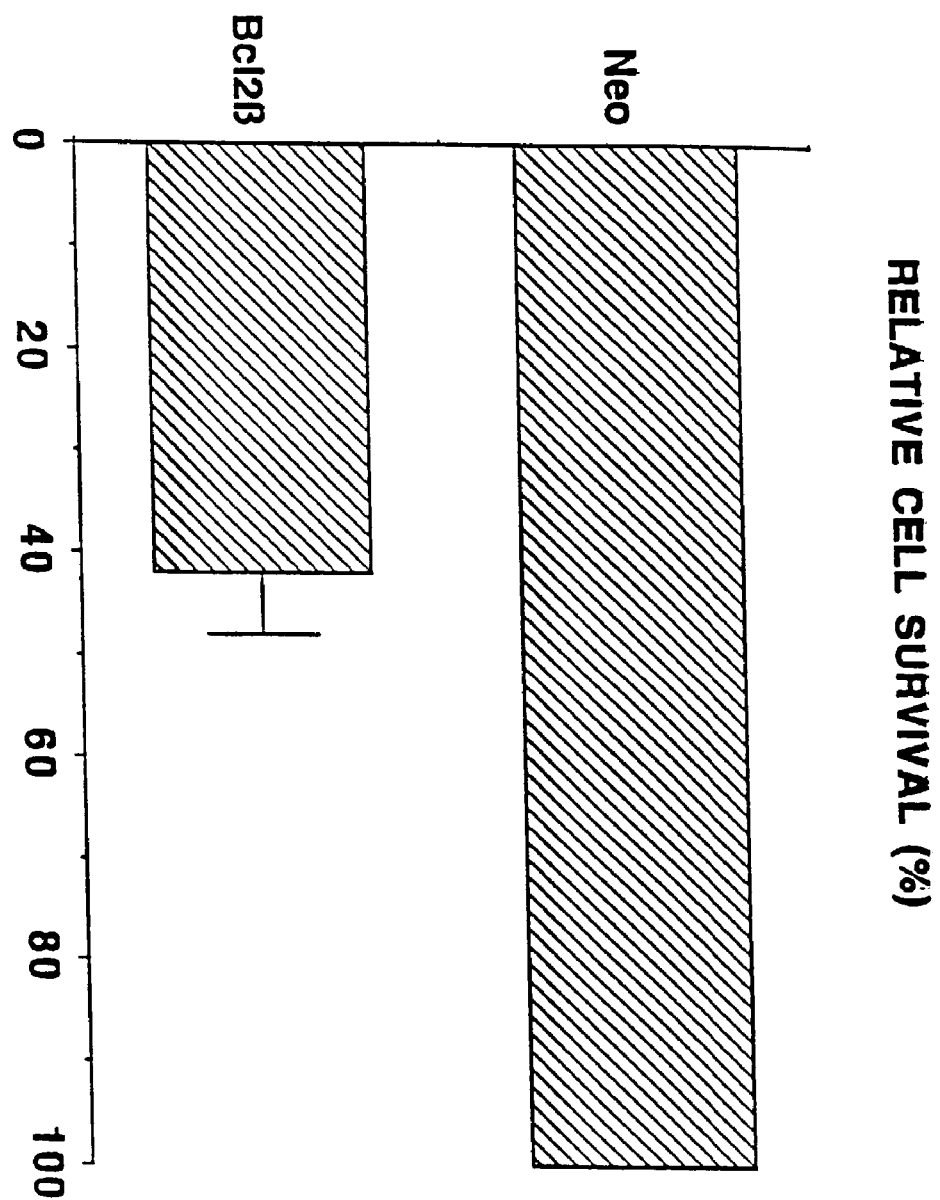

FIG. 7. A dominant-negative form of the Bcl-2 protein, Bcl-2β, accelerates cell death. Cell viability as determined by trypan blue exclusion. Data were normalized relative to the control cells (NEO) (mean +/− standard deviation of 4 determinations).

Figure 8:
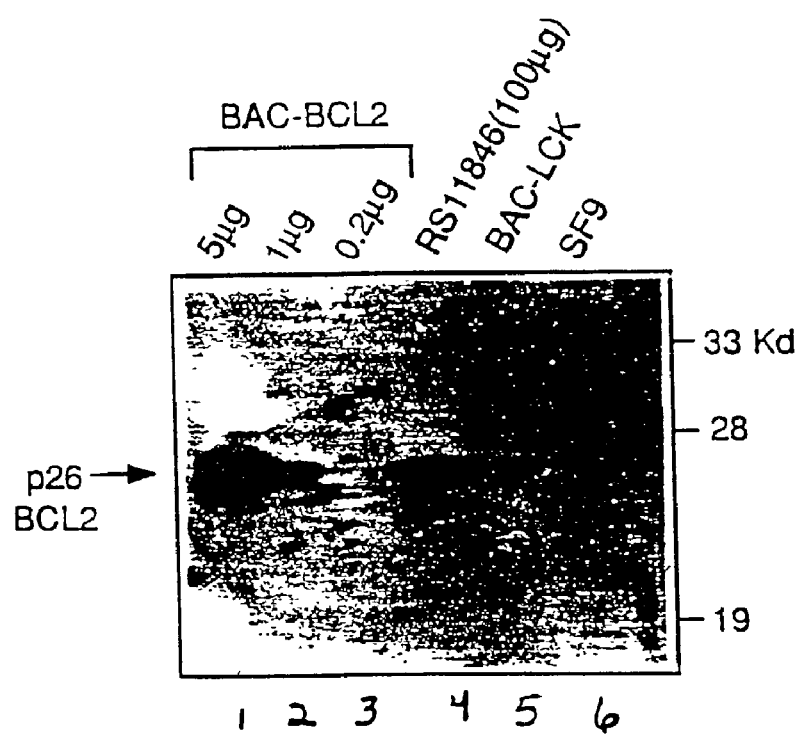

FIG. 8. Western blot of Sf9 cell extracts. Lanes 1-3 contain 5.0, 1.0 or 0.2 µg, respectively, protein from recombinant Bcl-2 baculovirus-infected cells; lane 4, 100 µg protein from t(14;18)-containing human B cell lymphoma cell line; lane 5, 10 µg protein from recombinant Lck baculovirus-infected cells (negative control); lane 6, 10 µg protein from uninfected cells.

Figure 9A:
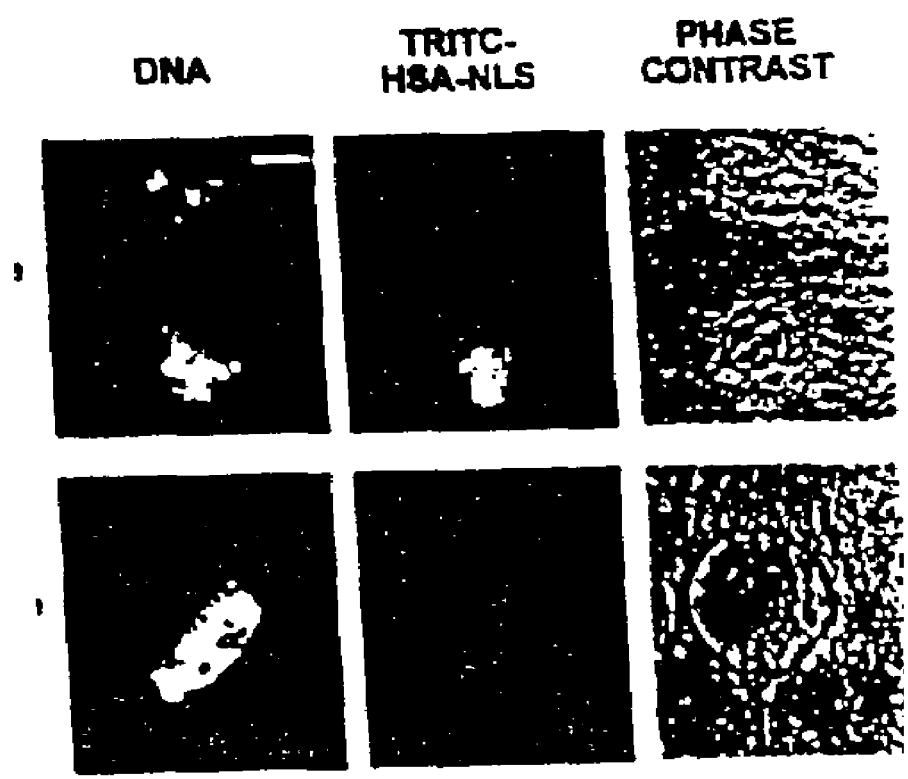
Figure 9B:
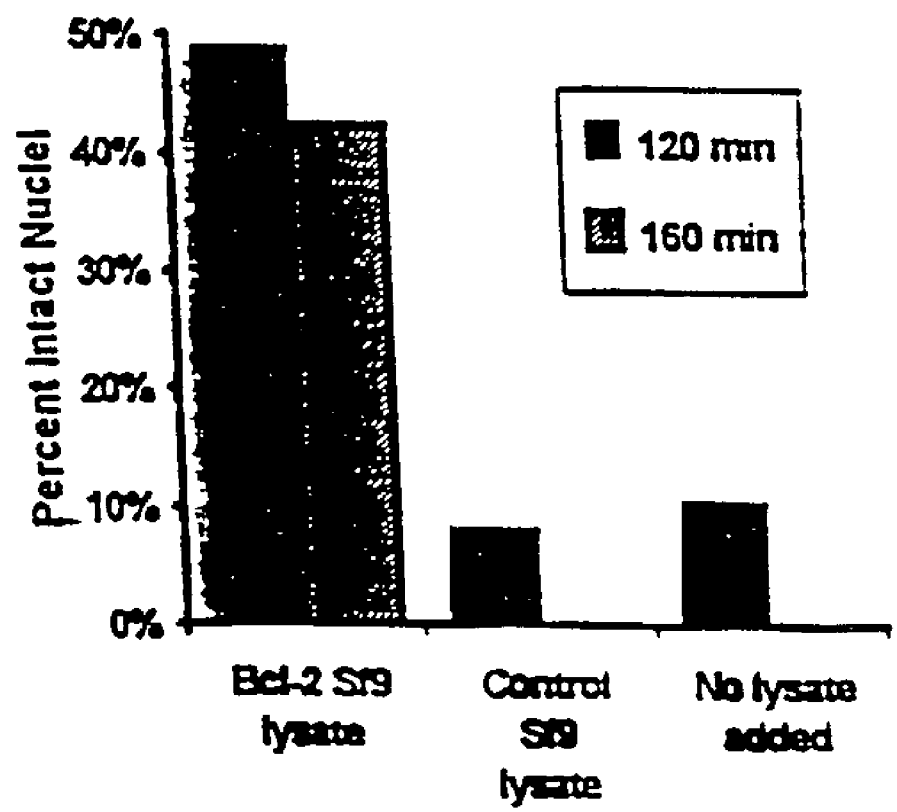

FIG. 9. Cell-free assay for assessing Bcl-2 function.

A. Nuclei incubated in cell free extracts containing Sf9 insect cell lysates prepared from control (upper panels) or Bcl-2-expressing (lower panels) Sf9 cells. Nuclei visualized using Hoechst 33258 DNA stain (DNA); tetramethylrhodamine-labeled BSA conjugated to a synthetic peptide corresponding to the nuclear localization signal of SV40 T-antigen (TRITC-HSA-NLS); phase contrast microscopy (PHASE CONTRAST).

B. Quantitation of intact, transport-competent nuclei incubated for 120 or 160 min in the presence of absence of Bcl-2.

Figure 10:
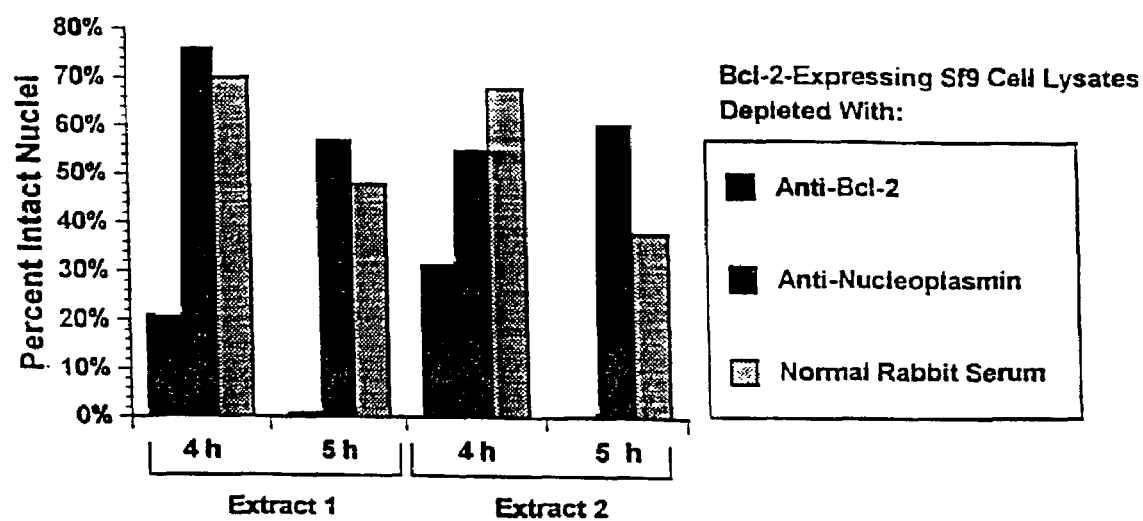

FIG. 10. Bcl-2 protein is directly responsible for suppression of nuclear breakdown in cell-free apoptosis assays.

DETAILED DESCRIPTION OF THE INVENTION

This invention is directed to general and effective methods to augment the treatment of diseases and pathological conditions. The methods are applicable to the treatment of cancer, neurodegenerative disorders, viral infections, autoimmune diseases and also to the modification of transplanted tissues and cells. The modified tissues and cells can be used, for example, in the treatment of neurological disorders, as well as diseases caused by hormonal and protein insufficiencies such as diabetes (insulin) and hemophilia (coagulation factors). The methods described herein also enable the development of novel pharmaceutics for the treatment and prevention of diseases and pathological conditions. Additionally, the methods of this invention can be further applied to the production of superior research and diagnostic reagents and compositions for use in essentially all disciplines of the basic and applied sciences.

The invention takes advantages of the ability of Bcl-2 to prevent the process of programmed cell death known as apoptosis. Targeting a physiological mechanism common to many diverse diseases is efficient and cost effective in that the specialized development of different drugs to each of the specific diseases is not required. Instead, a small number of therapeutic compounds or methods of treatment can be developed for the treatment of essentially all diseases that manifest their pathological condition through the aberrant regulation of apoptosis. In many cases, such compounds can be recombinant nucleic acids whose administration is by mode of gene therapy. Thus, reagents that either promote or impair apoptosis are used in the methods of the invention to retard disease-induced apoptotic cell death or to selectively enhance tumor cell killing by conventional chemotherapeutic drugs as well as to protect normal non-neoplastic cells from the toxicity of these drugs.

In one embodiment, gene transfer technology or "gene therapy" is used to create Bcl-2 recombinant DNA molecules and viral vectors to promote the in vivo survival of cells affected by a disease or pathological condition that results in apoptotic cell death. Bcl-2 recombinant DNA molecules and viral vectors are also used to genetically modify cells prior to transplantation to prolong their in vivo survival time and, where applicable, to simultaneously correct protein deficiencies. The use of Bcl-2 to immortalize or prolong the survival rate of targeted cells is advantageous in that it does not block cellular differentiation and is essentially non-tumorigenic when expressed in either primary or established cells compared to other oncogenes. Specific examples of such therapies include the production of recombinant viruses that direct Bcl-2 expression to specific types of neurons and the administration such viruses to patients having Alzheimer's or Parkinson's diseases via direct injection into the brain or spinal fluid; the intracranial implantation of Bcl-2 expressing fetal neuronal precursor cells for the treatment of Parkinson's disease; the mass expansion of human Bcl-2 expressing cells in vitro for prolonging their in vivo survival after transplantation and the use of recombinant vectors for directing Bcl-2 expression to specific cell types for the prevention of cell death induced by viral infections. Bcl-2-expressing cells for use in transplantations can be genetically modified, for example, to secrete various hormones and peptides such as neurotrophic factors in the setting of spinal cord injury, dopamine for the treatment of Parkinson's disease, enkephalins for pain control in terminally ill cancer patients, coagulation factors for patients with hemophilia and insulin producing islet cells for patients with diabetes.

In another embodiment, Bcl-2 gene transfer technology is used to "immortalize" human antibody-producing B-cells and thereby enhance the development of human monoclonal antibodies. The survival promoting function of Bcl-2 is also utilized to generate Bcl-2 transgenic mice for isolating B-cells for enhanced monoclonal antibody production. Such monoclonal antibodies are useful for diagnostic and therapeutic purposes.

In yet another embodiment, a cell-free system is described that faithfully reproduces characteristics of apoptotic cell death. The system is useful for the screening of compounds that alter the apoptotic process. Selected compounds that either promote or inhibit apoptosis can be used for therapeutic treatment of a variety of diseases including neurodegenerative diseases, cancer and virus infected cells.

The Bcl-2 gene was first discovered because of its involvement in lymphomas in humans. This gene has now been shown to prolong cell survival in culture when expressed at high levels in a variety of cell types such as lymphocytes, hemopoietic cells, fibroblasts and neurons. Bcl-2 is a 26 kilodalton (kDa) protein that is unique among cellular genes. It contains a stretch of 17 hydrophobic amino acids near its carboxy terminus that causes its post-translational insertion into intracellular membranes. Gene transfer studies have demonstrated that Bcl-2 promotes cell survival by blocking programmed cell death, or apoptosis.

Apoptosis can be actively triggered in cells by, for example, exposure to X-radiation, cytotoxic drugs, free-radicals and heat, or it can be unmasked by removal of critical peptide growth factors, steroid hormones, lymphokines or neurotrophins that constantly suppress programmed cell death in various tissues. Many of these processes are the terminal events involved in numerous disease states or the final events by which therapeutic treatments effect their results. Thus, to specifically target and alter apoptosis would provide a general treatment for a broad range of diseases and pathological conditions. It should be noted, however, that there exist Bcl-2-independent pathways for apoptosis. Thus, the new uses for Bcl-2 reported here constitute previously undocumented circumstances under which Bcl-2 gene transfer is revealed for the first time to exert protection against programmed cell death.

Bcl-2 is normally expressed in a variety of types of cells but particularly those that either exhibit a long lifespan such as some types of neurons, long-lived "memory" lymphocytes or cell having proliferative, self-renewing potential such as basal epithelial cells and hemopoietic progenitor cells in the bone marrow. It is likely that Bcl-2 represents the prototype of an entire family of structurally similar genes that are expressed in a tissue-specific manner and contribute to the regulation of cellular life span.

As used herein, the term "apoptosis" or "apoptotic cell death" refers to the physiological process known as programmed cell death. Apoptosis is unlike other forms of cell death that occur, for example, as the result of ischemia or necrosis because apoptosis is an active, ATP-requiring form of cell death that typically requires new RNA and protein synthesis. A hallmark of apoptosis is the activation of endogenous endonucleases that initially cleave the genomic DNA at its most accessible sites, i.e., between nucleosomes, producing a ladder of DNA bands representing integer multiples of the internucleosomal distance. This DNA degradation occurs early in the apoptotic process, before loss of plasma membrane integrity. Apoptotic cells also have a shrunken size and the process is not usually accompanied by inflammation since there is no spilling of cytoplasmic contents into the extracellular space. With apoptosis, much of the cell's content is autodigested. In vivo cell lysis never occurs because the apoptotic cells are usually phagocytosed by macrophages and related cells before loss of plasma membrane permeability. Consequently, there is no inflammatory reaction or subsequent scarring. Other morphological characteristics of apoptotic cells include nuclear fragmentation, development of vesicular bodies, "apoptotic bodies" and plasma membrane blebbing, all in the setting of intact mitochondria and lysosomes. Specific examples of apoptotic cell death as a natural programmed event include, for example, the loss of redundant neurons during fetal development and the destruction of potentially autoreactive T-cells during thymic education.

As used herein, the term "Bcl-2" refers to the protein originally discovered due to its inappropriate activation in lymphomas. Bcl-2 controls normal cell growth and differentiation by promoting cell survival. It has a molecular weight of about 26 kDa as determined by SDS-PAGE and is characterized by a hydrophobic stretch of about 17 amino acids near its carboxy terminus that functions in intracellular membrane attachment.

Bcl-2 has substantially the same amino acid sequence as that shown in GenBank accession M13994 and is encoded by a nucleotide sequence substantially similar to that shown as GenBank accession M13994. The definition of "Bcl-2" is intended to include other Bcl-2 family members such as those proteins that are found to exhibit the above functional characteristic or sequence homologies. Such members include, for example, homologs of Bcl-2 cloned from lower organisms such as rats, mice, chickens, flies and worms.

A specific example of a Bcl-2 family member is the protein encoded by the BHRF-1 gene in Epstein Barr virus. The BHRF-1 gene, which exhibits about 22% sequence identity and 47% sequence similarity with Bcl-2, is functionally equivalent to Bcl-2 in promoting cell survival (see, for example, FIG. 5).

It is understood that limited modifications to the protein can be made without destroying the biological function of Bcl-2 and that only a portion of the entire primary structure may be required in order to effect activity. For example, minor modifications of the Bcl-2 protein or nucleotide sequence which do not destroy its activity are included within the definition of Bcl-2. Moreover, fragments of Bcl-2 which retain at least one function of the entire protein are included within the definition. It is understood that various modifications of primary amino acid or nucleotide sequence may result in proteins having substantially equivalent or enhanced function as compared to the sequences set forth in GenBank accession number M13994. These modifications may be deliberate, as through site-directed mutagenesis, or accidental, such as through mutation in hosts which are Bcl-2 producers. All of these modifications are included as long as Bcl-2 biological function is retained. Furthermore, various molecules, such as other proteins, carbohydrates, or lipids, can be attached to Bcl-2. Such modifications are included within the definition of Bcl-2.

The invention provides a method of treating a disease or pathological condition resulting in apoptotic cell death. The method includes increasing the activity of Bcl-2 in cells affected by the disease or pathological condition. Diseases or pathological conditions can include, for example, neurodegenerative diseases, cancer and virus-infected cells.

Alzheimer's disease, the most common neurodegenerative disorder, is estimated to affect four million Americans and represents a major economic burden to families and society. No treatment can stop or even slow the progression of this disorder. Amyloid β-protein (ABP) has been identified as a possible causative agent of this disease. Addition of ABP, or of specific peptide fragments from this protein, to cultured neurons and neuronal cell lines results in cell death. Expression of Bcl-2 in these cultured cells by gene transfer can reduce neuronal cell killing by ABP. These results indicate that apoptosis contributes to neuronal cell death in Alzheimer's disease.

Parkinson's disease is a progressive and ultimately fatal neurodegenerative disorder characterized by loss of the pigmented dopaminergic neurons of the substantia nigra. The symptoms of Parkinson's disease can often be managed initially by administration of L-DOPA, the immediate precursor of dopamine. However, reduced efficacy of L-DOPA treatment often occurs possibly because metabolism of the drug prevents effective delivery to the CNS. Programmed cell death has also been implicated to play an important role in this neurodegenerative disorder inasmuch as withdrawal of neurotrophic factors from neurons leads to cell death through a mechanism consistent with apoptosis. Moreover, the absence of inflammatory cells or scar formation in the brains of patients with Parkinson's disease indicates that striatal neuron death can occur through apoptosis as opposed, for example, to necrosis.

In addition to neurodegenerative disorders, apoptosis has been indicated to result in cell death from glutamate-induced neurotoxicity arising from conditions such as stroke and amyotrophic lateral sclerosis (ALS; "Lou Gehrig's disease"). Glutamate-induced toxicity occurs when glutamate is released from dying neurons in the brain at times of acute injury. Glutamate released by dying neurons in turn binds to specific receptors for glutamate on adjacent healthy neurons, triggering signals that set-off a complex series of biochemical events leading to apoptotic cell death.

Diseases and pathological conditions such as those described above and those that will be described below can be treated by increasing the activity of Bcl-2 in the cells affected by the disease or pathological condition. Increasing Bcl-2 activity in these affected cells will inhibit the apoptotic death of such cells and therefore reduce or prevent progression of the disease or pathological condition.

The activity of Bcl-2 can be increased by a variety of means, including, for example, increasing the Bcl-2 synthesis rate or decreasing the Bcl-2 degradation rate or modulating the ability of Bcl-2 to interact with other proteins that control the apoptosis process. Increasing the synthesis rate of Bcl-2 will result in elevated protein accumulation and thereby increase Bcl-2 activity within the cell.

An elevated synthesis rate can be achieved, for example, by using recombinant expression vectors and gene transfer technology to express a Bcl-2-encoding nucleic acid. Such methods are well known in the art and are described below with reference to recombinant viral vectors. Other vectors compatible with the appropriate targeted cell can accomplish the same goal and, therefore, can be substituted for recombinant viral vectors in the methods described herein. For example, recombinant adenoviruses having general or tissue-specific promoters can be used to drive Bcl-2 cDNA expression and to deliver Bcl-2 expression constructs into a variety of types of tissues and cells, including non-mitotic cells such as neurons in the substantia nigra of the brain (the region affected in Parkinson's disease) (La Salle et al., *Science* 259:988-990 (1993), which is incorporated herein by reference).

Alternatively, recombinant adeno-associated viruses can be used for this purpose, with the added advantage that the recombinant virus can stably integrate into the chromatin of even quiescent non-proliferating cells such as neurons of the central and peripheral nervous systems (Lebkowski et al., *Mol. Cell. Biol.* 8:3988-3996 (1988), which is incorporated herein by reference). Receptor-mediated DNA delivery approaches also can be used to deliver Bcl-2 expression plasmids into cells in a tissue-specific fashion using a tissue-specific ligand or antibody non-covalently complexed with DNA via bridging molecules (Curiel et al., *Hum. Gene Ther.* 3:147-154 (1992); Wu and Wu, *J. Biol. Chem.* 262:4429-4432 (1987), both of which are incorporated herein by reference). Direct injection of DNA (mammalian expression plasmids of various types) or of DNA encapsulated in cationic liposomes also can be used for stable gene transfer to non-dividing and dividing cells in vivo (Ulmer et al., *Science* 259:1745-1748 (1993), which is incorporated herein by reference). In addition, DNA transfer by the particle bombardment method can be used to transfer DNA into a variety of tissues (Williams et al., *Proc. Natl. Acad. Sci. USA* 88:2726-2730 (1991), which is incorporated herein by reference).

Moreover, recombinant expression vectors encoding Bcl-2 can also contain additional non-Bcl-2-encoding nucleic acids that are useful for the therapeutic treatment of a disease or pathological condition. For example, Bcl-2-encoding vectors can be constructed to encode enzymes used in the synthesis of dopamine when treating Parkinson's disease, for example, with the idea of simultaneously providing genes for enhancement of cell survival (Bcl-2) and cell function (dopamine-β-hydroxylase). Other examples are Bcl-2 plus recombinant DNA sequences engineered to allow for nerve growth factor secretion for sustaining the survival of the cholinergic neurons that are typically lost in Alzheimer's disease (Rosenberg et al., *Science* 242:1575-1578 (1988), which is incorporated herein by reference), Bcl-2 plus insulin for the treatment of diabetes or Bcl-2 plus encephalin for treatment of intractable pain. Whether other non-Bcl-2-encoding nucleic acids are also contained within a vector will depend on the disease and the therapeutic need. One skilled in the art will be able to determine such a need.

Viruses are very specialized infectious agents that have evolved in many cases to elude host defense mechanisms. Typically, viruses infect and propagate in specific cell types. The targeting specificity of viral vectors utilizes this natural specificity, in turn, to specifically target predetermined cell types and, thereby, introduce a recombinant gene engineered into the viral genome into the infected cell. The vector to be used in the methods of the invention will depend on desired cell type to be targeted. For example, if neurodegenerative diseases are to be treated by increasing the Bcl-2 activity of neuronal cells affected by the disease, then a vector specific for cells of the neuronal cell linage could be used. Such viral vectors include, for example, Herpes simplex virus-based vectors (Battleman et al., *J. Neurosci.* 13:941-951 (1993), which is incorporated herein by reference). Similarly, if a disease or pathological condition of the hematopoietic system is to be treated, then a viral vector that is specific for blood cells and their precursors, preferably for the specific type of hematopoietic cell, should be used. Such viral vectors include, for example, HIV-based vectors (Carroll et al., *J. Cell. Biochem.* 17E:241 (1993), which is incorporated herein by reference).

Moreover, such vectors can additionally be modified with specific receptors or ligands to modify or alter target specificity through receptor mediated events. These modification procedures can be performed, for example, using recombinant DNA techniques or synthetic chemistry procedures. Specific examples of viral vectors and their specificity include, for example, Herpes simplex virus for neuronal cell lineages, HIV for T lymphocytes, hepatitis virus for liver cells and Adenovirus for lung and other tissues. In cases where viral infections cannot be made tissue-specific, it may be possible to make viral gene expression specific for only the desired type of cell through the use of tissue-specific promoters and enhancers (Dai et al., *Proc. Natl. Acad. Sci. USA* 89:10892-10895 (1992), which is incorporated herein by reference).

Viral vectors commonly used for in vivo targeting and therapy procedures are retroviral vectors or DNA-based vectors. Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. However, oncogenic transformation properties of these viruses are destroyed. Once the viral proteins are synthesized, the host cell packages the RNA into new viral particles, which can undergo further rounds of infection. The viral genome is also engineered to encode and express the desired recombinant gene.

In the case of non-infectious viral vectors, the helper virus genome is usually mutated to destroy the viral packaging signal, which is required to encapsulate the RNA into viral particles, but retains the structural genes required to package the co-introduced recombinant virus containing a gene or genes of interest. Without such a signal, any particles that are formed will not contain a genome and, therefore, cannot proceed through subsequent rounds of infection.

The methods for constructing and using such viral vectors are known in the art and are reviewed, for example, in Miller and Rosman, *Biotechniques* 7:980-990 (1992), which is incorporated herein by reference. The specific type of vector will depend upon the intended application. The actual vectors are also known and readily available within the art or can be constructed by one skilled in the art.

Bcl-2-encoding viral vectors can be administered in several ways to obtain expression and, therefore, increased activity of Bcl-2 in the cells affected by the disease or pathological condition. If viral vectors, for example, are used, the procedure can take advantage of their target specificity and the vectors need not be administered locally at the diseased site. However, local administration can provide a quicker, more effective treatment. Administration can also be by intravenous or subcutaneous injection into the subject. Injection of the viral vectors into the spinal fluid can also be used as a mode of administration, especially in the case of neurodegenerative diseases. Following injection, the viral vectors will circulate until they recognize host cells with the appropriate target specificity for infection.

An alternate mode of administration of Bcl-2 encoding vectors can be by direct inoculation locally at the site of the disease or pathological condition. Local administration is advantageous because there is no dilution effect and, therefore, a smaller dose is required to achieve Bcl-2 expression in a majority of the targeted cells. Additionally, local inoculation can alleviate the targeting requirement needed with other forms of administration since a vector can be used that infects all cells in the inoculated area. If expression is desired in only a specific subset of cells within the inoculated area, then promoter and expression elements that are specific for the desired subset can be used to accomplish this goal. Such non-targeting vectors can be, for example, viral vectors, viral genomes, plasmids, phagemids and the like. Transfection vehicles such as liposomes can be used to introduce the non-viral vectors described above into recipient cells within the inoculated area. Such transfection vehicles are known to one skilled within the art.

The Bcl-2 encoding nucleic acid used in the methods of the invention is known in the art and available from Genbank under the locus identification "HUMBCL2A" as accession number M13994. The nucleotide sequence available from the above database is all that is necessary for one skilled in the art to obtain a Bcl-2 cDNA for use in the disclosed methods. Moreover, since the Bcl-2 cDNA has been published in Tsujimoto and Croce, *Proc. Natl. Acad. Sci. USA,* 83:5214-5218 (1986), which is incorporated herein by reference, it is also readily available to those skilled in the art.

Using the Bcl-2 sequence described in GenBank accession number M13994, one skilled in the art can clone the Bcl-2 using conventional library screening methods. Oligonucleotide probes useful for screening can be synthesized using known methods in the art such as phosphoramidite chemistry. Other methods such as the polymerase chain reaction (PCR) also can be used to rapidly and efficiently clone Bcl-2-encoding nucleic acids. Using PCR, a DNA segment of up to approximately 6,000 base pairs in length can be amplified from a single gene copy.

Briefly, PCR involves incubating a denatured DNA sample with two oligonucleotide primers that direct the DNA polymerase-dependent synthesis of complementary strands. Multiple cycles of synthesis are performed, wherein each cycle affords an approximate doubling of the amount of target sequence. Each cycle is controlled by varying the temperature to permit denaturation of the DNA strands, annealing the primers and synthesis of new DNA strands. Use of a thermostable DNA polymerase eliminates the necessity of adding new enzyme for each cycle and permits fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202 all of which are incorporated herein by reference.

The invention also provides a method of treating a disease or pathological condition resulting in apoptotic cell death by increasing the activity of Bcl-2 wherein the disease or pathological condition is mediated by viral infection. The methods described above for the treatment of neurological diseases and pathological conditions can also be applied to various other disease states such as virus-infected cells. Many viral infections, such as HIV, culminate in cell death through apoptosis.

Apoptosis can be prevented or retarded by expressing a Bcl-2 encoding nucleic acid or functional equivalent thereof in viral-infected cells (see, for example, FIG. 3). Elevated levels of Bcl-2 inhibit the programmed cell death induced by an infecting viruses and result in prolonged survival of the infected cells. Bcl-2-containing viral vectors that appropriately target the infected cells can be used to specifically introduce and increase the Bcl-2 activity within the infected cells. Such vectors also can contain non-Bcl-2-encoding nucleic acids that are useful for treating the virus-infected cells.

The invention provides a method of prolonging the in vivo survival of transplanted cells for the treatment of a disease or pathological condition. The method includes increasing the activity of Bcl-2 in a population of cells and transplanting the population of cells having increased Bcl-2 activity into a subject. Diseases or pathological conditions can include, for example, neurodegenerative diseases, cancer and virus-infected cells.

The transplantation of genetically modified cells that secrete proteins, hormones or neurotransmitters, for example, can be used to treat the above diseases as well as many chronic, metabolic and inherited disorders such as diabetes and hemophilia. Employing the methods described herein, the in vivo survival of such diseased cells can be improved by Bcl-2 gene transfer. An advantage of treating cells using Bcl-2 is that Bcl-2 is not oncogenic in most cells and, therefore, can be used to "immortalize" cells that would be responsive to normal growth control mechanisms in vivo.

Cell transplantation is now being explored for the treatment of certain diseases, notably Parkinson's disease. For example, potential therapies in animal models of Parkinson's disease have included cell transplantation of genetically modified fibroblasts, which produce L-DOPA in the vicinity of the substantia nigra. Although the results of these experiments have been encouraging, the survival time of the transplanted cells is limited and, therefore, results in only a temporary and minor improvement of the condition.

Transplantation of fetal brain cells, which contain precursors of the dopaminergic neurons, has also been examined as a potential treatment for Parkinson's disease. In animal models and in patients with this disease, fetal brain cell transplantations have resulted in the temporary reduction of motor abnormalities. Furthermore, it appears that the implanted fetal dopaminergic neurons form synapses with surrounding host neurons. However, the transplantation of fetal brain cells is again limited due, for example, to the limited survival time of the implanted neuronal precursors.

In the specific case of Parkinson's disease, intervention by increasing the activity of Bcl-2 can improve the in vitro and in vivo survival of fetal and adult dopaminergic neurons, their precursors and dopamine-secreting fibroblasts and, thus, can provide a more effective treatment of this disease. Likewise, improved in vivo survival of essentially any cell type to be transplanted will improve the treatment of that disease. For example, neuronal cells or their precursors can be used for the treatment of other neurodegenerative diseases such as Alzheimer's disease and glutamate-induced neuronal cell death by enhancing the in vivo survival of cells using Bcl-2.

Specific examples of cell types other than neuronal cells include hepatocytes for the treatment of liver failure, β cells for the treatment of insulin-dependent diabetes and skin cells for the treatment of burns. Additionally, Bcl-2 expression can be used to enhance survival of transplanted cells for cosmetic treatments. One example of such a cosmetic purpose is for the treatment of alopecia, the medical term for baldness. Moreover, viral vectors can be employed using the methods that target Bcl-2 expression to the cells of the hair follicle or Bcl-2 transfer vehicles can be applied topically to the scalp, resulting in a novel genetic treatment for hair loss.

Cells to be transplanted for the treatment of a particular disease can be genetically modified in vitro so as to increase the activity of Bcl-2. Such methods are known within the art and are essentially the same as those described above, except that Bcl-2 expression is first achieved within the cells in vitro. Bcl-2-expressing vectors can be constructed using recombinant DNA techniques and can utilize, for example, viral vectors, viral genomes, plasmids, phagemids and the like (see, for example, FIG. 1). Such vectors can also encode one or more non-Bcl-2 nucleotide sequences to facilitate the therapeutic function of the cells once they are transplanted.

Bcl-2-encoding vectors are introduced into recipient cells using transfection methods known to one skilled in the art. Such methods include, for example, infection using viral vectors, lipofection, electroporation, particle bombardment and transfection. Detailed procedures for these methods can be found in Sambrook et al., *Molecular Cloning: A Laboratory Manual* (Cold Spring Harbor Laboratory Press, 1989) and the references cited therein, which are incorporated herein by reference.

Following transfection, cells having increased levels of Bcl-2 activity are selected for use in transplantation treatment. The screening procedure will depend on the method by which the Bcl-2 activity is increased. For example, if increased activity is accomplished through elevated Bcl-2 protein levels, then a quantitative assay that determines the accumulated Bcl-2 protein level can be used. Such assays include, for example, immunoblot analysis, immunoprecipitation and ELISA. Such methods are known to one skilled in the art and can be found in Ausubel et al., *Current Protocols* in *Molecular Biology* (John Wiley and Sons, 1989) or in Harlow et al., *Antibodies: A Laboratory Manual* (Cold Spring Harbor Laboratory Press, 1988), both of which are incorporated herein by reference. Functional assays also can be employed such as the inhibition of apoptotic DNA degradation or nuclear disintegration, such as disclosed herein or known in the art (see Example VII).

Similar to the use of Bcl-2 for prolonged in vivo survival of transplanted cells, the expansion of mammalian cells in culture for subsequent transplantation or the expansion of cells for industrial scale production of proteins, metabolites or other clinically useful factors can benefit from the enhanced survival due to Bcl-2. Among the limitations that plague these types of procedures are the dependence of many cell types on adherence to a solid surface. Moreover, many types of cells die through apoptosis when their required growth factors run in short supply or when toxic by-products accumulate in cultures of cells grown at high densities. Such problems can be overcome by increasing the levels of Bcl-2 within the cultured cells.

For example, increased levels of Bcl-2 can allow anchorage-dependent cells to survive and grow in the absence of attachment to a solid surface. Bcl-2 overexpression can also allow cells to grow to higher densities when compared to cells expressing low or normal Bcl-2 levels. Moreover, a novel form of the Bcl-2 protein, Bcl2/P59S, is substantially more active than the wild-type protein in allowing higher density growth and preventing cell death due to the depletion of growth and survival factors in tissue culture medium (FIG. 2). All of these properties of Bcl-2 can be utilized for mass expansion of cells in culture.

The invention also provides a method of prolonging the in vivo survival of transplanted cells for the treatment of a disease or pathological condition by increasing the Bcl-2 activity of immune cells. The immune system consists of a variety of cell types that protect the body from infectious organisms and continually monitor the body for the appearance of abnormal cells such as cancer cells. Some immune cells have the capacity to bind to and kill other cell types, particularly tumor cells and virus-infected cells. One outcome of the killer cell response, besides target cell death, is the activation of apoptosis within the killer cells, themselves. The physiological role of this self-induced suicide may be a negative feedback mechanism for controlling an immune response. However, this regulatory mechanism of immune cell death prevents immune responses from being of sufficient duration and intensity to effectively eliminate malignant or virus-infected cells. Tumor-specific and virus-specific immune cells can also die from lack of sufficient growth factors such as interleukin-2 (Il-2) in vivo. This process can be arrested or prevented by Bcl-2 gene transfer. Thus, the augmentation of immune cell survival due to increased Bcl-2 expression can result in more effective treatment of cancer and virus-induced diseases.

Apoptotic death of immune cells can be inhibited by isolating these cells or their precursors and modifying them to express elevated levels of Bcl-2. The methods for modifying these cells are essentially the same as those described above. The transplantation of the Bcl-2-expressing cells into a subject suspected of having a cancer or a viral infection will ensure a more prolonged and active immune response against the condition. As an alternative to extracorporeal treatment, tissue-specific gene transfer and expression technology can be used to specifically increase Bcl-2 gene expression in the killer cells in vivo.

Other non-Bcl-2 genes that augment the cell survival function of Bcl-2 or enhance the killer activity of immune cells can be introduced into cells in combination with Bcl-2. A specific example of introducing a second gene that enhances the effector activity of immune cells is the coexpression of the Lck protein tyrosine kinase. When constitutively overexpressed, for example, by mutation of the regulatory tyrosine residue at amino acid position 505 to a phenylalanine (Y505F), Lck confers T cell effector functions on the Y505F-expressing cell in the absence of IL-2. Abrogation of the IL-2 requirement is clinically advantageous because side effects due to treatment with an immunostimulatory drug such as IL-2 can be avoided. Nucleic acids encoding proteins other than Lck can be coexpressed to enhance effector functions of immune cells. Such nucleic acids include, for example, Lyn, Hck, Fyn, Yes, Atk, Fgr and Blk.

Raf-1, which encodes a serine-threonine protein kinase, is an example of a non-Bcl-2 gene that can be administered in conjunction with Bcl-2 to enhance the action of Bcl-2 (see Example V nd FIG. 6). Infection of cells with DNA sequences encoding a mutant version of the Raf-1 kinase having constitutive, non-inducible kinase activity acts synergistically with Bcl-2 to prolong cell survival by blocking apoptotic cell death (see, for example, FIG. 6.A.). Thus, coexpression of non-Bcl-2 genes to augment function of Bcl-2 or to enhance other desired functions provides a means of preventing or limiting virus infections and malignant cell growth.

The invention also provides a method for enhancing the sensitivity of malignant or virus-infected cells to therapy by decreasing the activity of Bcl-2 in the malignant or virus-infected cells. Decreased activity can be accomplished by expressing an alternative form of Bcl-2 capable of forming a bound complex with Bcl-2, wherein the bound Bcl-2 is inactive, or with other proteins that interact with Bcl-2, thus inhibiting the normal function of Bcl-2.

Many types of malignant cells become resistant or refractory to treatment due to high endogenous levels of Bcl-2. These malignant cells having high levels of Bcl-2 include prostate, colorectal and nasopharyngeal cancers and lymphomas, leukemias and neuroblastoma. Similarly, virus-infected cells can be intrinsically resistant to treatment because of endogenous Bcl-2 expression. In contrast to the previously described methods for increasing the Bcl-2 activity, such diseases can be effectively treated by utilizing the opposite approach, i.e., inhibiting Bcl-2 activity. Suppression of Bcl-2 function can be employed alone or in combination with conventional therapies to provide a more effective means of decreasing the resistance of malignant or virus-infected cells to killing by chemotherapeutic drugs and irradiation.

Bcl-2 expression can be inhibited, for example, by targeting and/or expression vectors that produce the alternative form of the Bcl-2 protein, Bcl-2β. When expressed in conjunction with a normal Bcl-2 gene, Bcl-2β binds to the cellular proteins with which Bcl-2 normally interacts and prevents Bcl-2 function, probably through a competition mechanism. The inhibition of a wild-type function through the coexpression of a variant form of a gene product is known in the art as a dominant negative mutation (FIG. 7; see, also, Kolch et al., *Nature* 349:426-428 (1991), which is incorporated herein by reference.

Bcl-2β arises through an alternative splicing mechanism and lacks the hydrophobic stretch of amino acids found in the normal Bcl-2 protein, the hydrophobic region being necessary for membrane insertion of Bcl-2 and its function as a blocker of apoptosis. Other examples of mutant Bcl-2 are proteins that have been genetically engineered to contain deletions within the region of amino acids 85-219 of the 239 amino acid Bcl-2 protein. In malignant cells where Bcl-2 function has been markedly reduced by dominant negative mutation, enhanced sensitivity to killing by a wide variety of chemotherapeutic drugs such as methotrexate, Adriamycin, Ara-C and dexamethasone can be observed.

In addition to inhibiting Bcl-2 activity to enhance the sensitivity of malignant or virus infected cells to therapy, other non-Bcl-2 gene products involved in the progression of the diseased state can be inhibited to increase the efficacy of treatment. For example, high levels of Raf-1 kinase activity are associated with radioresistance of tumors. Gene transfer manipulations that cause an increase of decrease of Raf-1 kinase activity can increase or decrease, respectively, the sensitivity of tumor cells to killing by chemotherapeutic drugs. Moreover, elevations in Raf-1 activity in the presence of increased Bcl-2 activity indicate that the combined use of reagents designed to interfere with Raf-1 and Bcl-2 can act synergistically to render tumor cells more sensitive to killing by conventional chemotherapeutic drugs and irradiation (see Example V).

As an alternative to gene therapy and transfer approaches, chemical compounds that alter the activity of Bcl-2 can be used. The same rationale as described above for treating diseases or pathological conditions can be applied to these applications, except that the specific compounds that alter the Bcl-2 activity are substituted in place of recombinant methods. Thus, all the therapies described previously using Bcl-2 gene transfer are equally applicable to the use of Bcl-2 specific compounds.

Novel Bcl-2 specific compounds can be obtained, for example, through rational design or random drug-screening methods. All that is required is a method to accurately identify active compounds. Active compounds include both those that increase Bcl-2 activity as well as those that decrease its activity. Thus, the determination of an activity will depend on the desired outcome.

The invention provides a method to identify compounds that alter the process of apoptosis (see Example VII). This method includes treating an apoptotic cell extract with one or more compounds and selecting the compound that alters the apoptotic process in the cell extract. Thus, the method allows the identification of active Bcl-2 specific compounds. The method consists of a cell free extract that faithfully reproduces the apoptotic process. Briefly, when *Xenopus* egg extracts are mixed with sperm chromatin, the chromatin is assembled into a nucleus that is surrounded by a nuclear enveloped. These cell free nuclei undergo degeneration spontaneously with time or inducibly in the presence of particular drugs. The nuclear degeneration process is indicative of the process that occurs in cells dying by apoptosis. Addition of Bcl-2 protein to the extracts prevents nuclear breakdown (see, for example, FIG. 9). Active Bcl-2 specific compounds can be identified by substituting the compound for Bcl-2 in the cell free extract. An advantage of the cell free extract method is that it can be automated by monitoring, for example, the transport of radiolabeled or fluorescent-tagged peptides into nuclei; this transport process is prevented by nuclear breakdown.

The invention also provides a method to enhance monoclonal antibody production by prolonging the in vitro survival of hybridoma precursor cells by increasing the activity of Bcl-2 in the precursor cells. Similar to the methods described above, Bcl-2 can enhance the survival, for example, of antibody producing cells. Such enhanced survival can increase the efficiency of monoclonal antibody production by allowing the generation of a greater number of successful fusions.

Precursor hybridoma cells, such as myeloma fusion partners and antibody-producing B cells, can be modified using methods described herein to elevate the expression of Bcl-2. Bcl-2 expression vectors can be introduced in vitro into the myeloma cells using the disclosed methods. Since the antibody-producing B cells are isolated from an immunized animal, increasing Bcl-2 expression in these cells can be accomplished by immunizing transgenic animals expressing a Bcl-2 encoding transgene. B cells taken from the spleen of such immunized animals will have enhanced survival characteristics compared to B cells from normal animals. Thus, the invention also provides transgenic mice expressing Bcl-2 as the transgene. Moreover, increased Bcl-2 activity can also be used to immortalize human B cells for the production of human monoclonal antibodies.

The following examples are intended to illustrate, but not limit the invention.

EXAMPLE I

This Example shows that Bcl-2 expression results in an increased number of viable 32D-3 cells in culture and allows the cells to remain viable for longer than normally observed for this cell line.

32D-3 cells were stably transfected with expression plasmids containing a G418 antibiotic resistance gene and either a wild-type or mutant human Bcl-2 DNA sequence. The mutant Bcl-2 sequence encodes a variant Bcl-2 protein having a serine substitution for a proline at amino acid position 59 (BCL2/P59S). This amino acid substitution results in a high level of constitutive expression of BCL2/P59S.

Following selection of the cells for G418 resistance, cells were plated and their viability was determined. As shown in FIG. 2.A., the number of viable control cells (Neo) reached a maximum about day 4-5, then decreased. The number of viable cells expressing the wild-type Bcl-2 protein (W.T.) also reached a maximum at about day 4-5, but the number of viable cells did not decrease during the time examined. In contrast, the number of viable cells expressing the variant Bcl-2 protein (P59S) increased for 6 days to a level about twofold greater than the control cells and the cells expressing with the wild-type Bcl-2 protein. As shown in FIG. 2.B., the number of viable cells is correlated to the level of DNA synthesis in the various populations of cells.

These results indicate that Bcl-2 causes an increase in the number of viable cells in culture and allows the cells to remain viable for a longer period of time than normal.

EXAMPLE II

This Example illustrates the effectiveness of Bcl-2 at preventing Sindbis virus-induced death of prostate cancer cells.

A rat prostate cancer cell line, AT-3, was infected with pZIP-BCL2 or pZIP-NEO (see FIG. 1.B.), then grown in the presence or absence of Sindbis virus. At various times after the addition of Sindbis virus, cells were collected and cell viability was determine using trypan blue exclusion.

As shown in FIG. 3, Sindbis virus infection resulted in the death of essentially all of the AT-3 cells within 3 days (solid circles). In contrast, AT-3 cells that expressed Bcl-2 were protected from Sindbis virus-induced death (solid squares) and survived as if no Sindbis virus was present (compare controls, open circles). These results show that Bcl-2 expression protects cells from death due to virus infection.

EXAMPLE III

This Example demonstrates the effectiveness of Bcl-2 for inhibition of glutamate-induced apoptosis in cultured neuronal PC12 cells.

Glutamate is released from dying neurons in the brain during stroke and other conditions where neuronal cell survival is compromised including, perhaps, ALS. Neurons contain cell surface glutamate receptors that appear to transduce poorly characterized signals leading to apoptotic cell death. In vitro studies have shown that glutamate treatment can result in the death of cultured cortical neurons and PC12 cells. Glutamate-induced cell death induced is accompanied by internucleosomal DNA degradation and ultrastructural changes resulting from apoptosis. Bcl-2 expression protects neuronal cells from glutamate-induced cell death.

The rat pheochromocytoma cell line, PC12, was stably infected with pZIP-BCL-2 or pZIP-NEO (see FIG. 1.A.), then treated with 30 mM glutamate for 24 hours. Following treatment, cell viability was assessed by MTT dye reduction assay as described in Tada et al., *J. Immunol. Meth.* 93:157-165 (1986). As shown in FIG. 4, Bcl-2 expression protected the PC12 cells from glutamate-induced death.

PC12 cells or other neuronal cell lines that are sensitive to treatment with glutamate can be infected with recombinant Bcl-2. High level production of the human Bcl-2 protein is confirmed by immunoblotting. The resulting cell lines are cultured with various concentrations of glutamate. After various times, cells are recovered from culture and DNA fragmentation is assessed by qualitative gel-electrophoresis assays and by quantitative biochemical methods.

A sample of cells are fixed and embedded for electron microscopic analysis to determine whether ultrastructural changes indicative of apoptosis occurs. The percentage of viable cells also is compared for Bcl-2-expressing and control cells using a version of the MTT dye reduction assay or by recovering the cells from cultures using 20% pancreatin, resuspending them in medium containing propidium iodide and determining the percentage of viable cells by fluorescence microscopy or by fluorescent activated cell sorting.

A qualitative DNA fragmentation assay is performed using the gel electrophoresis assay described in Sorenson et al., *J. Natl. Canc. Inst.* 82: 749 (1990). In addition, quantitative DNA fragmentation assays are performed. Briefly, cells are grown for 12-24 hours in medium containing 1 µCi/ml 3H-thymidine to metabolically radiolabel the cellular DNA. Cells are washed three times and approximately $1 \times 10^6$ are returned to their usual culture media. The cells are incubated in the presence of various concentrations of glutamate (0-50 mM). Four to 24 hours later, the cells are pelleted by centrifuged and the culture supernatant is collected to determine the $^3$H-thymidine concentration by liquid scintillation counting (fraction 1).

The cells are resuspended in 5 mM Tris (pH 7.4), 10 mM EDTA, 0.5% Triton X100 and centrifuged at 13,000×g for 30 min. The radioactivity in the resulting supernatant (fraction 2), which contains low molecular weight (fragmented) DNA, and the pellet, which contains intact high molecular weight DNA (fraction 3), is determined. The percentage of DNA fragmentation is calculated by summing the counts per minute (cpms) of radioactivity in fractions 1 and 2, and dividing by the total cpms of radioactivity in all three fractions.

EXAMPLE IV

This Example demonstrates the similarity of action of viral and avian homologs of human Bcl-2.

32D-3 cells were stably transfected with expression plasmids containing either a hygromyin (HYG) or a G418 (NEO) antibiotic resistance gene and cDNA encoding either the human Bcl-2 protein, the chicken Bcl-2 protein or the BHRF-1 protein from Epstein Barr Virus (viral homolog of Bcl-2). Production of the desired proteins or the corresponding mRNA was verified by immunoblot or northern blot assays. Following transfection, cells were cultured without growth factor for various times and the number of viable cells was determined.

As shown in FIG. 5.A., the chicken Bcl-2 homolog was nearly as effective as the human Bcl-2 in prolonging cell viability in culture. Similar results were observed for the viral BHRF-1 protein, which also increased cell viability in the absence of growth factors (FIG. 5.B.). Cell proliferation studies demonstrated that the increase in viability was not, in fact, due to cell growth.

EXAMPLE V

This Example demonstrates that non-Bcl-2 proteins involved in cell survival act synergistically to prolong survival of 32D-3 cells in vitro.

32D-3 cells were stably transfected with expression plasmids producing Bcl-2 protein, activated Raf-1 protein or both Bcl-2 and Raf-1, then cultured under conditions of growth factor deprivation that cause apoptosis. At various times after removing the growth factor from the medium, cells were collected and viability was determined.

As shown in FIG. 6.A., the expression of Raf-1 alone had no effect on cell survival, whereas expression of Bcl-2 alone had a modest effect. Remarkably, expression of both Bcl-2 and Raf-1 proteins together resulted in synergistic prolongation of cell survival. Significantly, no difference was observed in the level of DNA synthesis of the various populations of cells (FIG. 6.B.), indicating that the combined effect of Bcl-2 and Raf-1 represents enhanced cell survival and not, for example, an ability to proliferate in the absence of growth factors.

Flow cytometry was used to confirm that the growth factor-deprived cells were not proliferating. Cells were grown for 3 days in the presence or absence of Il-3. Following incubation, cells were stained with propidium iodide and the relative DNA content of the cells was determined. As shown in FIG. 6.C., BCL2-expressing cells and BCL2/RAF-expressing cells grown in the presence of growth factor (panels a and c) exhibit similar patterns of fluorescence intensity, as do the different cell lines grown in the absence of Il-2 (panels b and d). The reduction in the number of cells having a higher DNA content is consistent with the greater number of non-cycling $G_0/G_1$-phase cells present in the cells grown in the absence of Il-3 (panels b and d).

EXAMPLE VI

This Example illustrates the effectiveness of a dominant-negative form of the Bcl-2 protein in accelerating 32D-3 cell death.

Figure 1A:
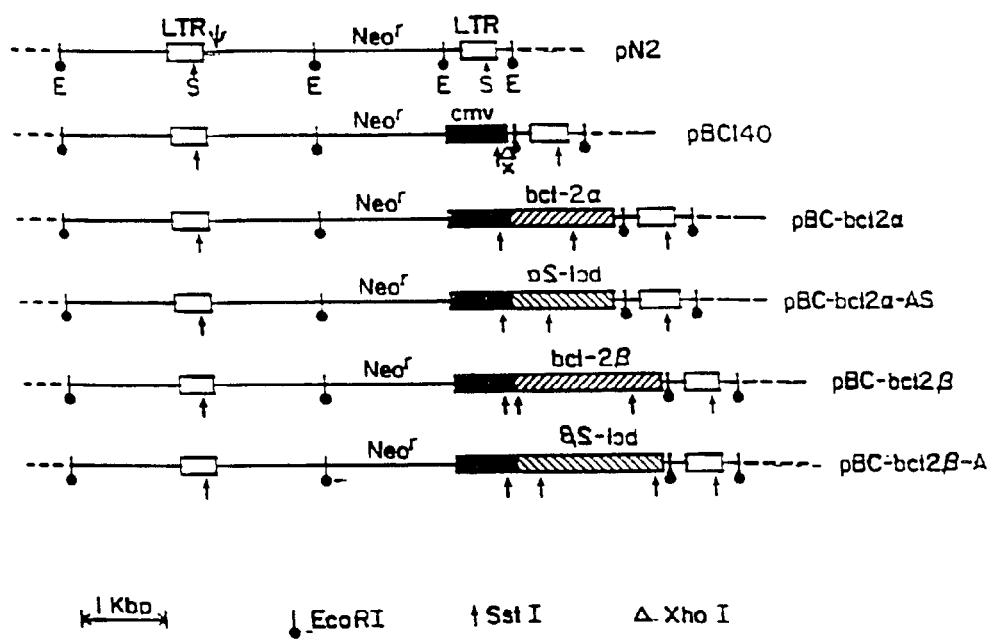
FIG. 1. Recombinant Bcl-2 retroviral vectors constructed using standard recombinant DNA techniques.
Figure 1B:
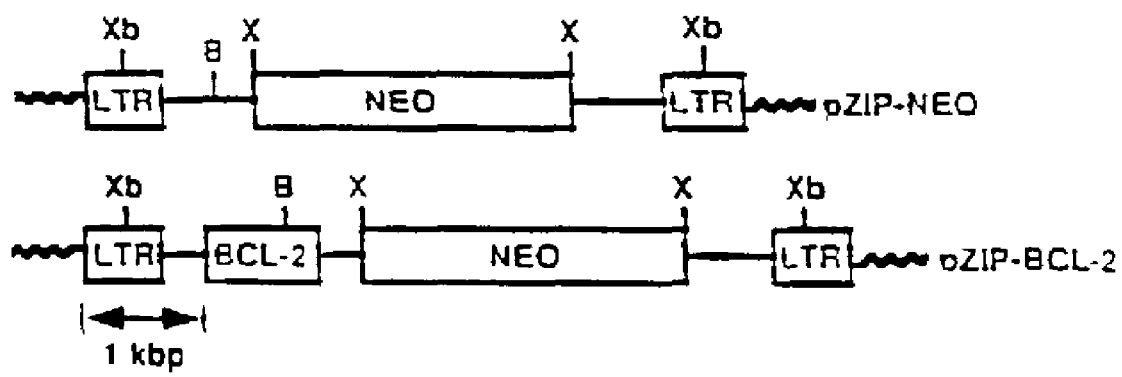

32D-3 cells were stably infected with retrovirus vectors containing a gene conferring neomycin resistance alone or in combination with a DNA sequence encoding a 22 kDa form of the Bcl-2 protein, Bcl-2β (FIG. 1.A.). Following infection, cells were cultured for 1 day without growth factor and the number of viable cells was determined. As shown in FIG. 7, expression of the dominant-negative Bcl-2β protein resulted in a significant cell killing.

EXAMPLE VII

This Example shows that Bcl-2 inhibits apoptotic degradation of nuclei in a cell free system.

A cell-free assay for assessing Bcl-2 function was developed to rapidly screen compounds for ability to inhibit or enhance Bcl-2 protein function. The assay utilizes in vitro self-assembled nuclei generated by mixing cell extracts derived from *Xenopus laevis* eggs with isolated sperm chromatin. The nuclei assemble normally but, after about 2 hours, begin to disintegrate. The nuclei appeared contracted and had the same appearance as isolated nuclei that had been treated briefly with an endonuclease. This phenomenon appears to represent apoptosis. Alternatively, isolated hepatocyte nuclei can be substituted for sperm chromatin and mixed with the egg extracts, resulting in the same phenomenon.

To test the effect of Bcl-2 protein on nuclei, lysates were prepared from Sf9 insect cells infected with recombinant baculoviruses encoding either Bcl-2 or an irrelevant protein such as β-galactosidase (β-gal) or the Lck kinase (see Reed et al., *Anal. Biochem.* 205:70-76 (1992). To confirm that Bcl-2 was expressed in the insect cell lysates, Sf9 insect cells were infected with recombinant Bcl-2 baculovirus or recombinant Lck baculovirus vectors. Infected cells were incubated for three days to allow expression of the gene products, then lysates were obtained and fractionated by SDS-PAGE electrophoresis. Following electrophoresis, proteins were transferred to membrane and probed with an antiserum raised against a synthetic peptide corresponding to part of the predicted amino acid sequence of human Bcl-2. As shown in FIG. 8, Bcl-2 protein was expressed in Sf9 cells infected with the Bcl-2 baculovirus vector (lanes 1 and 2) but not in uninfected cells (lane 6) or cells infected with a baculovirus expressing the Lck kinase (lane 5). Bcl-2 protein comprised about 5-10% of the total extracted protein.

Sf9 cell lysates were added at a 1:90 dilution into the *Xenopus* extracts or to a final protein concentration of 10 μg/ml (see Newmeyer and Wilson, *Meth. Cell Biol.* 36:607-634 (1991), which is incorporated herein by reference). In extracts receiving the control Sf9 lysate, chromatin condensation began after about 2 hours (FIG. 9.A., upper panels, and FIG. 9.B.). Round, highly condensed bodies that stain brightly with the Hoechst 33258 DNA dye formed and general contraction of the nuclei and floating bits of condensed chromatin in the surrounding extract were apparent (not shown). After about another 40 min of incubation, the nuclei had disintegrated completely (FIG. 9.B.) and a generally dispersed filamentous background of Hoechst fluorescence remained along with many small spherical or irregularly shaped aggregates of chromatin (not shown).

In contrast, when the Bcl-2-containing lysate was added, the nuclei were protected from this kind of degradation (FIG. 9.A., lower panels, and FIG. 9.B.). A considerable proportion of the nuclei remained intact and were completely functional in nuclear transport of the fluorescent substrate, tetramethylrhodamine-labeled BSA conjugated to a synthetic peptide corresponding to the nuclear localization signal of SV40 T-antigen (TRITC-HSA-NLS). Note that in FIG. 9.A., the upper panels contain two nuclei, only one of which is intact and accumulates the fluorescent transport substrate. The lower panels (Bcl-2 present) show a typical intact nucleus, which has accumulated the transport substrate and has grown considerably, acquiring new membrane by fusion of nuclear membrane vesicles with the nuclear membrane. The DNA (FIG. 9. A., left panel) is concentrated in one part of the nucleus of the Bcl-2-treated extract. This DNA localization roughly corresponds with the original elongated shape of the sperm chromatin body and has a normal feathery, i.e., decondensed, appearance typical of the morphology of sperm nuclei assembled in standard, non-apoptotic *Xenopus* egg extracts.

Quantitation of the intact, transport-competent nuclei observed in a typical experiment revealed that, after 2 hours of incubation, about 50% of the nuclei in the Bcl-2-treated extracts were intact (in standard, non-apoptotic extracts the percentage of intact nuclei can range from 50-90%), whereas only 8-10% of the control nuclei were intact, as measured by transport competence (FIG. 9.B.). As discussed above, no intact nuclei remained 40 min later in the control extracts. However, 42% of the nuclei in extracts containing Bcl-2 remained intact and transport-competent after two hours and forty min incubation. Thus, the Bcl-2-containing lysates confer on nuclei in these extracts a protection from degradation.

In order to show that the suppression of nuclear breakdown was due to the presence of Bcl-2 protein, immunoprecipitation reactions were performed. Two different insect cell lysates were pre-incubated with anti-Bcl-2-specific antibodies or irrelevant antibodies prior to addition to the *Xenopus* cell free apoptosis assay. As shown in FIG. 10, lysates incubated with anti-Bcl-2 antibodies lost the ability to suppress nuclear degradation, whereas incubation with irrelevant antibodies had no effect on the ability of the lysates to suppress degradation. Depletion of Bcl-2 protein following immunoprecipitation of the lysates with anti-Bcl-2 antibody was confirmed by western blot analysis (not shown).

Additional results indicate that the action of Bcl-2 is not mediated through changes in the efficiency of nuclear import. Measurement of the nuclear import activity in these same samples showed that the addition of Bcl-2-containing lysate resulted in no gross changes in the amount of fluorescent transport substrate imported by nuclei in one hour.

As a result of the disclosure that nuclear lysis in the cell free system is mediated by a pathway that can be blocked by Bcl-2, the system can be used to examine compounds generated, for example, by rational design or random synthesis, for the ability to alter apoptosis. Compounds that exhibit the desired activity can be selected and used for treating various diseases and pathological conditions.

EXAMPLE VIII

This example shows that Bcl-2 expression vectors can be used to prolong the in vivo survival of genetically-engineered fibroblasts that secrete L-DOPA when transplanted into lesioned brains. A similar approach can be used when transplanting genetically modified myoblasts, neuroendocrine or other cell types. In addition, the vectors need not be directly injected but can be incorporated into biocompatible "capsules" that can be implanted into the desired region of the brain.

Bcl-2 gene transfer is used for prolonging the survival of intracranially implanted fibroblasts that are genetically engineered to secrete L-DOPA. An immortal rat fibroblast line (208F) or primary rat skin fibroblasts stably infected with tyrosine hydroxylase-encoding recombinant retroviruses has been grafted into the denervated striatum of rat brains. These transplanted cells reduce behavioral symptoms for 2 and 10 weeks, respectively. The loss of a therapeutic effect after a few weeks for 208F cells was a result of the loss of surviving transplanted cells. In this animal model of Parkinson's disease, the success of the therapeutic approach has been hampered by the failure of transplanted fibroblasts to survive long-term in the brains of animals. The expression of Bcl-2 can circumvent this problem and prolong the intracranial survival of genetically engineered fibroblasts when transplanted into the striatum of brains.

To generate fibroblasts coexpressing Bcl-2 and tyrosine hydroxylase (TH), Bcl-2 retroviruses are used to infect established and primary rat fibroblasts that previously stably infected with viruses expressing TH. Bcl-2/TH positive cells are selected and stereotactically introduced into the brains of subjects having Parkinson's disease.

The methods for performing these injections in human patients are described, for example, in Freed et al., *New Engl. J. Med.* 327: 1549-1555 (1992) and Freed et al., *Arch. Neurol.* 47: 505-512 (1990). Briefly, before the operation, the caudate and putamen are visualized by CT scanning. Implantation is carried out through an elliptical craniectomy (3.5 by 1.5 cm) with the patient awake and sedated and under local anesthesia. The patient's head is mounted into a stereotactic frame and the CT scan is used to determine the coordinates for injection. Six to nine needle passes are made on each side of the brain and 1.5-3 µl of cell suspension is deposited along 10 mm tracks in the putamen, caudate or both as the needle is slowly withdrawn.

An animal model that can be used to test the efficacy or optimize the procedure is the use of rats, which have undergone 6-hydroxydopamine lesioning of their striatum neurons. For example, the in vivo lifespan of Bcl-2-expressing fibroblasts transplanted into the brains of such rats is compared with the lifespan of fibroblasts infected with control virus. In this way, the appropriate number of cells required for a particular Bcl-2-expressing cell line can be determined.

Experiments can be performed using the rat model. In this case, implantation is performed by mounting the anesthetized animal's head in a stereotactic frame and injecting 10 µl of cell suspension into two sites in the striatum using the coordinates AP=0.3 mm; ML=2.0 mm; DV=4.5 mm, and AP=1.5 mm; ML=2.0 mm, DV=4.5 mm, as described in Paxinos and Watson, *The Rat Brain in Stereotaxic Coordinates* (Academic Press, 1982). At each site, 2.5 µl of cells are dispensed, then the syringe is raised 1 mm and another 2.5 µl is administered at a rate of 1 µl/minute. The syringe is left in place for an additional 2 min to allow for diffusion of the cells, as described in Fisher et al., *Neuron* 6:371-380 (1991), which is incorporated herein by reference.

The retroviral vector used for stably infecting TH positive fibroblasts expresses both a Bcl-2 cDNA and the lacZ gene of *E. coli*. LacZ encodes the β-gal, which is easily monitored by calorimetric assays. The salient features of this vector include a Moloney sarcoma virus 5'-LTR followed by the Bcl-2 gene, an internal ribosome initiation site, lacZ and a 3' Moloney leukemia virus LTR. This retroviral construct results in significantly higher titers of virus production than the popular pBAG vector (see Austin and Cepko, *Development* 110:713-732 (1990), which is incorporated herein by reference).

To produce the viral vectors, the above-described plasmid will be transfected by standard calcium phosphate precipitation into PE501, an ecotrophic packaging cell line that has a lower incidence of spontaneous recombination events than the more commonly used Psi-2 cells. As used herein, the term "ecotrophic" means the viral vector has a limited host range, i.e., only infects rodent cell, as opposed to the term "amphotrophic," which refers to a virus than infects cells from all species. The transiently produced virus is used to stably infect the amphotrophic cell line PA317 by the method of Miller et al., *Som. Cell Mol. Gen.* 12: 175-182 (1986), which is incorporated herein by reference.

After 2 passages in culture to allow for viral integration, stably infected cells are enriched by three rounds of fluorescence activated cell sorting (FACS) using a fluorescent β-gal substrate that can be used with viable cells, Nolan et al., *Proc. Natl. Acad. Sci. USA* 85:2603-2607 (1988), which is incorporated herein by reference. Sorted cells are seeded at low density into cultures or plated at limiting dilution into microtiter plates. Individual clones are randomly recovered, propagated in culture and screened initially for virus expression based on relative levels of Bcl-2 protein production as determined by immunoblot assay using antibodies specific for human Bcl-2 protein.

Culture supernatants derived from promising clones are titered by infection of NIH3T3 cells and scored for foci of blue cells in monolayer cultures. This screening procedure uses a protocol that involves fixing the cells in situ and staining with calorimetric substrates for β-gal, Lim and Chae, *Biotechniques* 7:576-579 (1989), which is incorporated herein by reference. Clones exhibiting the highest virus production are then analyzed by DNA blot to verify integrity of the integrated provirus(es) and tested for contaminating helper virus by standard methods (see, for example, Mann et al., *Cell* 33:153-159 (1983), which is incorporated herein by reference).

To obtain the Bcl-2/TH positive fibroblasts, the Bcl-2/β-gal vector generated above is stably infected into TH positive rodent fibroblasts. The infected cells are enriched by flow cytometry and implanted into the 6-hydroxydopamine lesioned brains of rats. Treatment is monitored by weekly evaluation for symptoms such as apomorphine- or amphetamine-induced rotations. Animals are sacrificed at various times to determine the relative numbers of surviving cells by histochemical analysis of tissue sections stained blue by use of appropriate calorimetric substrates of β-gal.

An alternative approach to the above-described β-gal-dependent selection strategy for optimizing transplantation procedures is to use other retroviral vectors instead of the Bcl-2/β-gal vector. These other vectors contain, for example, an appropriate marker such as a hygromycin resistance gene, Gäken et al., *Biotechniques* 13:32-33 (1992), which is incorporated herein by reference. In this way, Bcl-2 cDNA is introduced into G418-resistant, TH-expressing fibroblasts and the stably infected cells are selected for growth in hygromycin. Where a calorimetric marker gene is unavailable, the presence of Bcl-2 protein producing fibroblasts in the brains of rats is assessed, for example, by immunohistochemical means using anti-Bcl-2 antibodies, which are specific for the exogenous form of the protein and useful for immunostaining formalin- or Bouin's reagent-fixed, paraffin-embedded tissues.

EXAMPLE IX

This example shows the use of Bcl-2 expression vectors to prolong the in vivo survival of transplanted fetal dopaminergic neurons.

Bcl-2 gene transfer is used for prolonging the in vitro survival of dopaminergic neurons recovered from fetal neural tissues. Immortalized TH-expressing neuronal precursors were constructed using a v-myc retrovirus as the immortalizing oncogene. Fetal cells from the mesencephalic flexure region of day 13 rat embryos were used because the neuronal cells that populate the substantia nigra and subsequently innervated the striatum are thought to migrate through this area around gestational day 12 to 14, Marchlard and Poirier, *Neuroscience* 9:373-381 (1983), which is incorporated herein by reference.

Cells were infected with a v-myc virus and placed into culture. By 12 days post infection, all of the uninfected control cells were dead, whereas about half of the cells exposed to v-myc virus survived. After selection in G418, cells were cloned and propagated in culture for at least 20 passages over 6 months. Three clones were selected at random for detailed characterization and one of them, termed MF13/H11, was found to contain TH.

As shown by immunohistochemical studies, MF13/H11 cells expressed typical neuronal cell antigens such as the 150 kDa and 200 kDa neurofilament proteins, a neuron-specific adhesion protein, contactin, and a marker of the neural crest, ganglioside GD2. The cells did not express the glial cell and astrocyte markers GFAP and the proteoglycan NG2. The cells continue to divide in high-density conditions when provided with serum but atrophy and die when serum is withdrawn. MF13/H11 is the first immortalized dopaminergic neuronal precursor clone described to date.

Although there is some reported success using v-myc or temperature-sensitive versions of SV40 large T antigen for immortalization of neuronal precursor cells and subsequent differentiation of these cells in vivo, the immortalized clones that retain ability to differentiate are the exception rather than the rule. The TH-expressing MF13/H11 cells described above, for example, exhibit little ability to differentiate in vitro when stimulated with retinoic acid and other potent pharmacological inducers of neuronal cell differentiation. Unlike v-myc, however, Bcl-2 has the capacity to immortalize cells without affecting their ability to proliferate and differentiate.

To prolong the in vitro survival of fetal neuronal cells, the same procedure described above for the immortalization of these cells with v-myc is used except that Bcl-2 is used instead. Both an ecotrophic (PE501) and an amphotrophic cell line (PA317) are used to insure that any preferences will be avoided.

Briefly, infections are performed by culturing the fetal neuronal precursor cells for 1-2 days in tissue culture dishes coated with poly-L-lysine or poly-L-ornithine. Such conditions eliminate glial cells and favor the attachment of neuronal precursor cells. High-titer ($>10^6$ colony forming units/ml) virus-containing supernatants are collected from fresh cultures of PA317 or PE501 cells and added to the fetal cell cultures for 3 to 4 hrs with 10 to 20 μg/ml polybrene or for 16-24 hrs with 4 μg/ml polybrene. Virus-containing media is then removed and the fetal cells are cultured for 1 to 2 days longer before adding the appropriate selection agent (G418, hygromycin or puromycin depending on whether a neomycin phosphotransferase, hygromycin phosphotransferase or puromycin-resistance gene, respectively, was included in the recombinant bcl-2 retrovirus). Continued culture in media containing these antibiotics can be for as little as 1 day or for several months, depending on the goals of the experiment.

In some cases, no selection with antibiotics is performed. Here, selection of Bcl-2 infected cells is essentially performed using the survival-promoting functions of Bcl-2. Only Bcl-2 virus-infected cultures will contain viable, proliferating cells since uninfected mesencephalic cells typically are dead within two weeks. Alternatively, β-gal activity, Bcl-2 RNA or protein analysis can be used to screen for Bcl-2-expressing neuronal precursor cells. The Bcl-2 stable transformants are expanded and transplanted essentially as described above for the fibroblasts.

EXAMPLE X

This Example describes the production of transgenic mice expressing Bcl-2.

The DNA construct used for the production of Bcl-2 transgenic mice was constructed as follows. A 4.3 kb fragment (λ1032-5/SH) containing a portion of the human Bcl-2 3' untranslated region, t(14;18) breakpoint, heavy chain joining region gene segment and the IGH enhancer region was excised from the λ phage clone λ1032-5 (Tsujimoto et al., Science 229:1390-1393 (1985), which is herein incorporated by reference) by digestion using SstI and HindIII. The excised sequence was made blunt-ended using DNA polymerase (Klenow fragment) and T4 polymerase and subcloned into the HincII site of pSKII (Stratagene, La Jolla, Calif.). A 6.9 kb fragment (p18-21H/BH) containing two promoters and the first two exons and a portion of the second intron of Bcl-2 was excised from p18-21H by Hind III and partial BamHI digestion and subcloned into the pSKII/$E_\mu$ plasmid above, Tsujimoto et al., Proc. Natl. Acad. Sci. USA 84: 1329-1331 (1987), which is herein incorporated by reference. Finally, a 4.4 kb HindIII fragment (p18-4/H) containing a portion of the second intron, third exon, 3' untranslated region and polyadenylation site of Bcl-2 was isolated from p18-4 and subcloned into the HindIII site located between the 5' Bcl-2 and, $E_\mu$ fragments described above. For microinjection, a 13-kb DNA fragment was isolated from the final plasmid by BssHII digestion, gel purified and dialyzed against modified TE buffer (10 mM Tris-HCl, pH 7.5., 0.1 mM EDTA).

Transgenic mice were produced by injecting about 250-500 copies of the above construct into the male pronucleus of (SWR/J×SJL/J) $F_1$ fertilized eggs by standard methods known in the art. Integration of the transgene was initially screened by PCR analysis of tail lysates using primers specific for the t(14;18) major breakpoint region. Results were confirmed by DNA blot analysis of liver DNA isolated from $F_1$ progeny of each transgenic line. All backcrosses were with SWR/J mice. Relative levels of Bcl-2 protein were measured by a two-step immunoprecipitation/immunoblot assay that uses antibodies specific for the human Bcl-2 protein, as described in Reed et al., Canc. Res. 51:6529-6538 (1991).

Although the invention has been described with reference to the disclosed embodiments, it should be understood that various modifications can be made without departing from the spirit of the invention. Accordingly, the invention is limited only by the following claims.

What is claimed is:

1. A method for monoclonal antibody production, comprising increasing the activity of Bcl-2 in a B cell in vitro by introducing and expressing a nucleic acid molecule encoding Bcl-2/P59S or BHRF-1 in said B cell, thereby prolonging the in vitro survival of said B cell, and fusing said B cell with a myeloma cell to generate a monoclonal antibody producing hybridoma cell.

2. The method of claim 1, wherein said B cell is a mouse B cell.

3. The method of claim 1, wherein said B cell is a human B cell.

4. The method of claim 1, wherein said nucleic acid molecule encodes Bcl-2/P59S.

5. The method of claim 1, wherein said nucleic acid molecule encodes BHRF-1.

6. The method of claim 1, further comprising introducing into said B cell a nucleic acid molecule encoding Raf-1.

7. The method of claim 1, further comprising introducing into said B cell a nucleic acid molecule encoding a polypeptide selected from Lck, Lyn, Hck, Fyn, Yes, Atk, Fgr, and Bik.

8. A method for monoclonal antibody production, comprising obtaining a B cell from a transgenic mouse, wherein said B cell expresses Bcl-2/P59S or BHRF-1 from a transgene, wherein expression of Bcl-2/P59S or BHRF-1 prolongs the survival of said B cell; and fusing said B cell with a myeloma cell to generate a monoclonal antibody producing hybridoma cell.

9. The method of claim 8, wherein said transgenic mouse is immunized with a predetermined antigen.

10. The method of claim 8, wherein said B cell expresses Bcl-2/P59S.

11. The method of claim 8, wherein said B cell expresses BHRF-1.

12. The method of clam 8, wherein said B cell is isolated from the spleen or other lymphoid organs of said immunized transgenic mouse.

* * * * *